United States Patent
Nishino et al.

(10) Patent No.: US 8,901,316 B2
(45) Date of Patent: Dec. 2, 2014

(54) PROCESS FOR PREPARING AMINOADAMANTYL CARBAMATE DERIVATIVES

(75) Inventors: Yutaka Nishino, Amagasaki (JP);
Hideki Shimizu, Amagasaki (JP);
Takayuki Tsuritani, Toyonaka (JP);
Natsuko Suzuki, Amagasaki (JP);
Mutsumi Takaki, Amagasaki (JP);
Tatsuya Kobayashi, Amagasaki (JP);
Hideaki Sakamoto, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 122 days.

(21) Appl. No.: 13/816,120

(22) PCT Filed: Aug. 8, 2011

(86) PCT No.: PCT/JP2011/068031
§ 371 (c)(1),
(2), (4) Date: Mar. 27, 2013

(87) PCT Pub. No.: WO2012/020724
PCT Pub. Date: Feb. 16, 2012

(65) Prior Publication Data
US 2013/0197240 A1  Aug. 1, 2013

(30) Foreign Application Priority Data
Aug. 9, 2010 (JP) .................. 2010-178584
Mar. 17, 2011 (JP) .................. 2011-058939

(51) Int. Cl.
| C07C 269/06 | (2006.01) |
| C07C 269/08 | (2006.01) |
| C07C 271/34 | (2006.01) |
| C07D 231/14 | (2006.01) |
| C07C 269/02 | (2006.01) |
| A61K 31/415 | (2006.01) |

(52) U.S. Cl.
CPC ............ C07D 231/14 (2013.01); C07C 269/02 (2013.01); C07C 271/34 (2013.01); *C07C 2103/74* (2013.01); *C07B 2200/07* (2013.01); A61K 31/415 (2013.01); C07C 269/08 (2013.01); C07C 269/06 (2013.01)
USPC .......... 548/374.1; 560/162; 560/163

(58) Field of Classification Search
None
See application file for complete search history.

(56) References Cited

U.S. PATENT DOCUMENTS 6,166,063 A  12/2000  Villhauer
7,728,029 B2  6/2010  Anderson et al.

(Continued)

FOREIGN PATENT DOCUMENTS

EP  2088136  8/2009
EP  2221380  8/2010

(Continued)

OTHER PUBLICATIONS

Lavrova et al., "Some amino alcohols of the adamantane series and their derivatives," translated from Zhurnal Organicheskoi Khimii, 1976, vol. 12, No. 11, pp. 2369-2374.

(Continued)

*Primary Examiner* — Kamal Saeed
(74) *Attorney, Agent, or Firm* — Hamre, Schumann, Mueller & Larson, P.C.

(57) ABSTRACT

Disclosed is a process for producing an aminoadamantane carbamate derivative which is useful as a significant intermediate of an 11βHSD-1 inhibitor.
A process for producing an acid addition salt of a compound represented by the Formula (II):

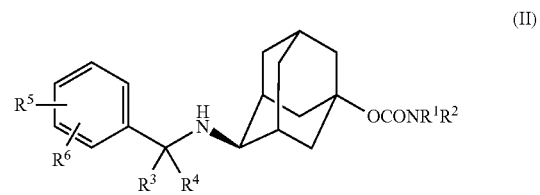

(II)

or a solvate of the acid addition salt, wherein $R^1$ and $R^2$ are each independently hydrogen, substituted or unsubstituted alkyl or the like; $R^3$ and $R^4$ are each independently hydrogen, substituted or unsubstituted alkyl or the like; and $R^5$ and $R^6$ are each independently hydrogen, halogen, carboxy, nitro, substituted or unsubstituted alkyl or the like;

which comprises separating an acid addition salt of a compound represented by the Formula (II) or a solvate of the acid addition salt by adding an acid to a mixture of syn isomer and anti isomer of a compound represented by the Formula (I):

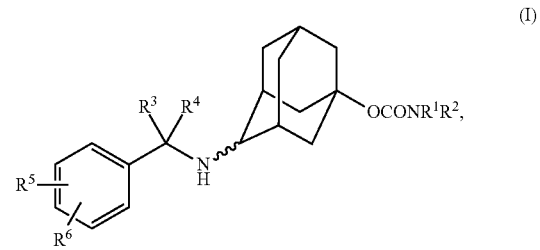

(I)

wherein $R^1$, $R^2$, $R^3$, $R^4$, $R^5$, and $R^6$ are as defined above, in the presence of a solvent.

29 Claims, 10 Drawing Sheets

(56) References Cited

U.S. PATENT DOCUMENTS

| | | |
|---|---|---|
| 8,507,493 B2 * | 8/2013 | Peddi et al. ............... 514/253.01 |
| 2006/0079506 A1 | 4/2006 | Linders et al. |
| 2008/0096869 A1 | 4/2008 | Linders et al. |
| 2009/0170832 A1 | 7/2009 | Kurose et al. |
| 2010/0105923 A1 | 4/2010 | Watanabe |
| 2010/0240659 A1 | 9/2010 | Masuda et al. |
| 2011/0009391 A1 | 1/2011 | Braun et al. |
| 2011/0086405 A1 | 4/2011 | Tomikawa et al. |
| 2011/0159019 A1 | 6/2011 | Tanaka et al. |
| 2011/0269971 A1 | 11/2011 | Watanabe |
| 2012/0259128 A1 | 10/2012 | Ogawa et al. |

FOREIGN PATENT DOCUMENTS

| | | |
|---|---|---|
| EP | 2345640 | 7/2011 |
| EP | 2518051 | 10/2012 |
| WO | 00/34241 | 6/2000 |
| WO | 2005/016877 | 2/2005 |
| WO | 2007/114125 | 10/2007 |
| WO | 2009/068531 | 6/2009 |
| WO | 2011/012800 | 2/2011 |
| WO | 2012/124781 | 9/2012 |

OTHER PUBLICATIONS

Klimova et al., "Hydroxyaminoadamantanes and their biological activity," Khimiko Farmatsevticheskii Zhurnal, 1986, vol. 20, No. 7, pp. 810-815, with English abstract.

Jaroskova et al., "An expeditious preparation of E-2-amino-5-hydroxyadamantane and its Z-isomer," Tetrahedron Letters, 2006, vol. 47, pp. 8063-8067.

Van Deursen et al., "Origin of anomalous shift additivity in rigid saturated molecules: NMR spectra of secondary substituted adamantanes, part III," Tetrahedron, 1971, vol. 27, issue 19, pp. 4593-600.

Villhauer et al., "1-[[(3-hydroxy-1-admantyl)amino]acetyle]-2-cyano-(S)-pyrrolidine: a potent, selective, and orally bioavailable dipeptidyl peptidase IV inhibitor with antihyperglycimic properties," Journal of Medicinal Chemistry, 2003, vol. 46, No. 13, pp. 2774-2789.

* cited by examiner

PROCESS FOR PREPARING AMINOADAMANTYL CARBAMATE DERIVATIVES

FIELD OF THE INVENTION

The present invention relates to a process for producing an aminoadamantyl carbamate derivative and an 11βHSD-1 inhibitor (11β-hydroxysteroid dehydrogenase type I inhibitor) using the above derivative.

BACKGROUND ART

An aminoadamantyl carbamate derivative is a useful compound as a pharmaceutical synthesis material or an intermediate. For example, the derivative can be used as a synthetic intermediate of a compound represented by the Formula (VIII):

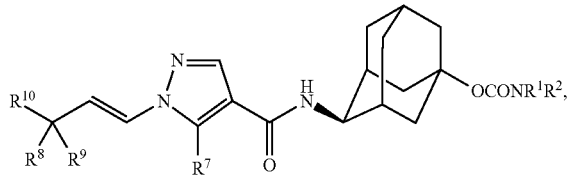

its salt, or a solvate thereof.

The compound represented by the Formula (VIII) has 11βHSD-1 inhibitory activity, and a pharmaceutical composition comprising the compound is known to be useful as a therapeutic agent for type II diabetes (Patent Document 1 and Patent Document 2).

Non Patent Document 1 describes a process for producing 1-hydroxy-4-aminoadamantane by a reaction such as Leuckart reaction from 1-hydroxy-4-adamantanone. The document states that, in the reaction, the ratio of the produced stereoisomer is advantageous for syn isomer, where the ratio of the amount of syn isomer produced to the amount of anti isomer produced is from 3:1 to 1:1.

Non Patent Document 2 describes a process for producing 1-hydroxy-4-aminoadamantane by performing hydroxylation of 2-aminoadamantane in a 1:10 mixture of nitric acid and sulfuric acid.

Entry 6 in Table 1 of Non Patent Document 3 describes a process of reacting 5-hydroxy-2-adamantanone with benzylamine in the presence of $H_2$/5% Pt—C, and states that the ratio of the stereoisomer produced in the reaction, i.e. the amount of anti isomer produced to the amount of syn isomer produced is 1:1. Moreover, Entry 8 in Table 2 states that the ratio of the amount of anti isomer produced to the amount of syn isomer produced of 2.7:1 can be obtained by reacting 5-hydroxy-2-adamantanone with benzylamine in the presence of $H_2$/5% Rh—C and Al (iOPr)$_3$. The production ratios of anti isomer to syn isomer in these two experimental examples were measured by $^1$H-NMR, and neither of the compounds was isolated.

Patent Document 3 describes a process for producing an anti isomer of 1-hydroxy-4-aminoadamantane, the process comprising reacting 5-hydroxy-2-adamantanone with L(−)-1-phenyl-ethylamine in the presence of a heterogeneous catalyst, for example, rhodium supported by carbon, purifying the resulting mixture of anti isomer and syn isomer with column chromatography, isolating the anti isomer and then debenzylating the anti isomer.

Patent Document 4 describes a process for producing an anti isomer, the process comprising reacting 5-hydroxy-2-adamantanone with ammonia/methanol in the presence of sodium borohydride, amidating the resulting mixture of anti isomer and syn isomer, and purifying the resulting amide body with column chromatography.

Patent Document 5 describes a process for producing an anti isomer, the process comprising amidating a mixture of anti isomer and syn isomer of 1-hydroxy-4-aminoadamantane with carboxylic acid and purifying the resulting amide body with column chromatography.

However, none of the documents describe a process for preparing an aminoadamantyl carbamate derivative and a compound represented by the Formula (VIII) using the above derivative. Moreover, in the process described in any of the documents, the produced mixture of anti isomer and syn isomer needed to be purified with column chromatography, and thus the process was industrially difficult to apply.

Patent Document 6 describes a process for producing 1-hydroxy-4-aminoadamantane, the process comprising setting 5-hydroxy-2-adamantanone and benzylamine derivative to a reductive aminating reaction, obtaining preferentially an anti isomer by crystallization purification from the produced mixture of anti isomer and syn isomer, followed by deprotection. The document states that the ratio of the amount of anti isomer to the amount of syn isomer of the 1-hydroxy-4-aminoadamantane produced by the process is from 13:1 to 50:1. However, the document does not describe a process for preparing an aminoadamantyl carbamate derivative of the present invention and a compound represented by the Formula (VIII) using the above derivative.

PRIOR ART DOCUMENT

Patent Document

PATENT DOCUMENT 1: WO2007/058346
PATENT DOCUMENT 2: WO2008/142986
PATENT DOCUMENT 3: WO2004/056745
PATENT DOCUMENT 4: WO2005/108368
PATENT DOCUMENT 5: WO2005/016877
PATENT DOCUMENT 6: WO2008/053652

Non-Patent Document

NON PATENT DOCUMENT 1: Zhurnal Organicheskoi Khimii 1976, 12(11), 2369
NON PATENT DOCUMENT 2: Khimiko Farmatsevticheskii Zhurnal 1986, 20(7), 810
NON PATENT DOCUMENT 3: Tetrahedron Letters 47 (2006) 8063

DISCLOSURE OF INVENTION

Problems to be solved by the Invention

The present invention provides an efficient process for producing an aminoadamantyl carbamate derivative useful as a pharmaceutical synthetic material or an intermediate. More specifically, the present invention provides a process for producing an aminoadamantyl carbamate derivative which is a useful intermediate in efficiently preparing a compound represented by the Formula (VIII):

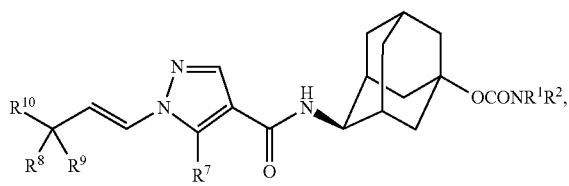

(VIII)

its salt, or a solvate thereof.

Moreover, the present invention provides a process for producing a compound represented by the Formula (VIII), its salt, or a solvate thereof using the intermediate.

Means for Solving the Problem

The inventors of the present invention found that, as an efficient process for producing an aminoadamantyl carbamate derivative, an anti isomer could be highly purified by crystallization, by way of reacting a compound represented by the Formula (IV):

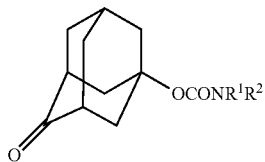

(IV)

and a benzylamine derivative represented by the Formula (V):

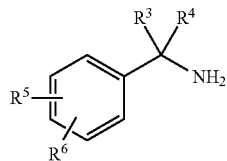

(V)

in the presence of a reducing agent, followed by making the resulting mixture of anti isomer and syn isomer into an acid addition salt. The inventors found that, by making the mixture into an acid addition salt, the difference in solubility to a solvent between anti isomer and syn isomer and the difference in crystallization, i.e. the ease to crystallize, are developed, and thus an acid addition salt of the anti isomer or a solvate of the acid addition salt may be preferentially precipitated. The inventors also found that, by debenzylating the resulting anti isomer, the anti isomer of an aminoadamantyl carbamate derivative can be prepared with high purity.

The inventors also found that, a compound represented by the Formula (III):

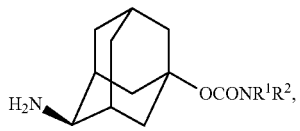

(III)

its salt, or a solvate thereof is useful as a synthetic intermediate for a compound represented by the Formula (VIII), its salt, or a solvate thereof. By using the intermediate, a compound represented by the Formula (VIII), its salt, or a solvate thereof can be efficiently prepared.

The process described in the prior art document is to produce a compound represented by the Formula (IX):

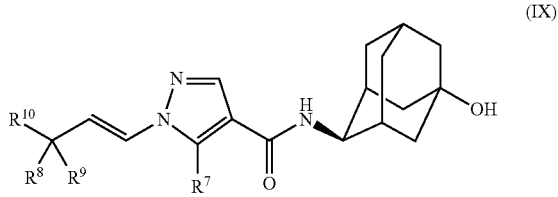

(IX)

followed by modifying a hydroxyl group on an adamantane skeleton.

This process requires further reaction of a compound represented by the Formula (IX) produced by multisteps as material, thus it may prove to be uneconomical depending on the yield of the modifying reaction to be followed and the number of steps involved to prepare the end object.

Moreover, a compound represented by the Formula (IX) has low solubility and solvents that can be used are limited. Tetrahydrofuran (THF) is an example of a solvent capable of dissolving a compound represented by the Formula (IX), but it was discovered that there was a problem that chlorosulfonyl isocyanate (CSI) used to modify the hydroxyl group on the adamantane skeleton reacted with THF to form a polymer.

The inventors found that the compound represented by the Formula (VIII), its salt, or a solvate thereof can be efficiently produced by first synthesizing an adamantane amine derivative having an intended group, followed by reacting the derivative with a compound represented by the Formula (VII):

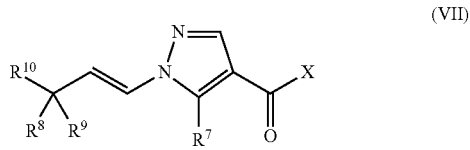

(VII)

as described in the present invention.

The inventors of the present invention completed the following invention.

(1)

A process for producing an acid addition salt of a compound represented by the Formula (II):

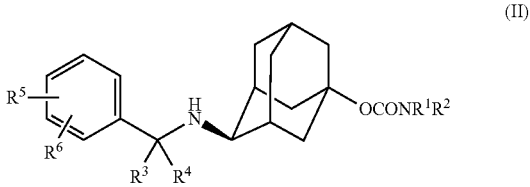

(II)

or a solvate of the acid addition salt, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl;

which comprises separating an acid addition salt of a compound represented by the Formula (II) or a solvate of the acid addition salt by adding an acid to a mixture of syn isomer and anti isomer of a compound represented by the Formula (I):

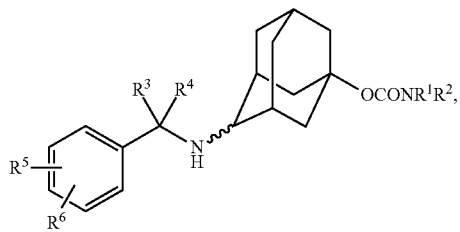

(I)

wherein $R^1$, $R^2$, $R^3$, $R^4$, $R^5$, and $R^6$ are as defined above, in the presence of a solvent.

(2)
The process according to the above (1), which comprises crystallizing an acid addition salt of a compound represented by the Formula (II) or a solvate of the acid addition salt.

(3)
A process for producing a compound represented by the Formula (III):

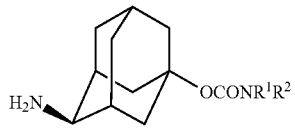

(III)

wherein $R^1$ and $R^2$ are as defined in the above (1), its salt, or a solvate thereof, which comprises deprotecting an acid addition salt of a compound represented by the Formula (II):

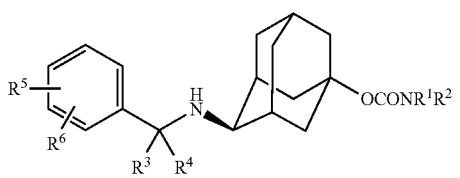

(II)

or a solvate of the acid addition salt, wherein $R^1$, $R^2$, $R^3$, $R^4$, $R^5$ and $R^6$ are as defined in the above (1).

(4)
The process according to the above (3), wherein the deprotection is performed in the presence of an acid.

(5)
The process according to the above (4), wherein the acid is hydrochloric acid.

(6)
The process for producing the compound represented by the Formula (III) according to the above (3), its salt, or a solvate thereof, which comprises the process according to the above (1) or (2).

(7)
The process according to any one of the above (1) to (6), wherein the acid addition salt is hydrochloride.

(8)
The process according to any one of the above (1) to (6), wherein the acid addition salt is benzoate.

(9)
The process according to any one of the above (1) to (6), wherein an acid addition salt of a compound represented by the Formula (II) or a solvate of the acid addition salt is a toluene-solvated benzoate.

(10)
A process for producing a compound represented by the Formula the (VI):

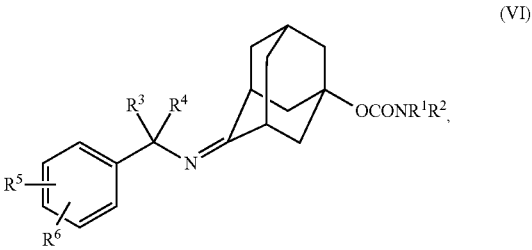

(VI)

its salt, or a solvate thereof, wherein $R^1$, $R^2$, $R^3$, $R^4$, $R^5$ and $R^6$ are as defined in the above (1) which comprises reacting a compound represented by the Formula (IV):

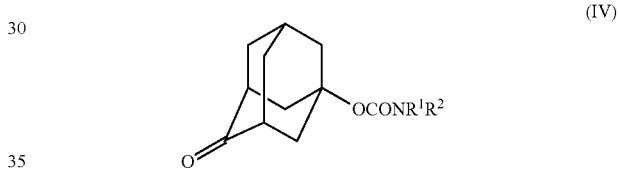

(IV)

wherein $R^1$ and $R^2$ are as defined in the above (1), and a compound represented by the Formula (V):

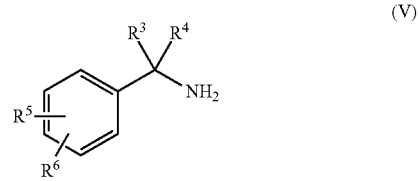

(V)

wherein $R^3$, $R^4$, $R^5$ and $R^6$ are as defined in the above (1).

(11)
A process for producing a compound represented by the Formula (I):

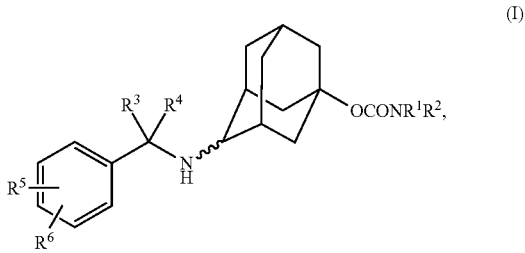

(I)

its salt, or a solvate thereof, wherein $R^1$, $R^2$, $R^3$, $R^4$, $R^5$ and $R^6$ are as defined in the above (1), which comprises reducing a compound represented by the Formula (VI):

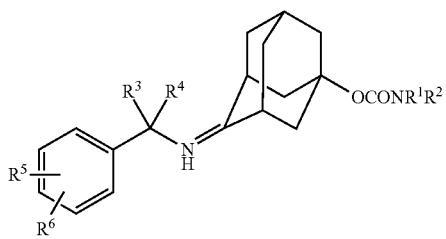

wherein $R^1$, $R^2$, $R^3$, $R^4$, $R^5$ and $R^6$ are as defined in the above (1).

(11-1)
A process for producing a compound represented by the Formula (I):

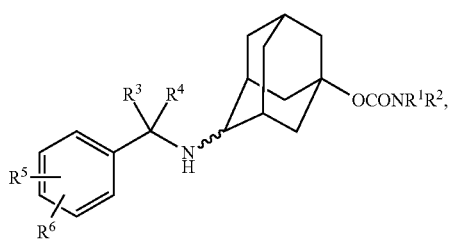

its salt, or a solvate thereof, wherein $R^1$, $R^2$, $R^3$, $R^4$, $R^5$ and $R^6$ are as defined in the above (1), which comprises reacting a compound represented by the Formula (IV):

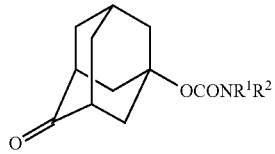

wherein $R^1$ and $R^2$ are as defined in the above (1), and a compound represented by the Formula (V):

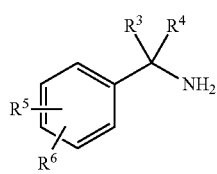

wherein $R^3$, $R^4$, $R^5$ and $R^6$ are as defined in the above (1) in the presence of a reducing agent.

(12)
The process according to any one of the above (10), (11) and (11-1), wherein the process comprises adding an acid.

(13)
The process according to any one of the above (11), (11-1) and (12), wherein a hydride reducing agent is used for reducing.

(14)
The process according to any one of the above (11), (11-1) and (12), wherein the process comprises reduction using one or more reducing agent(s) selected from sodium tri(acetoxy)hydroborate, sodium borohydride, lithium tetrahydroborate, pyridine borane complex, tetrahydrofuran borane complex, dimethyl sulfide borane complex, 2-picoline borane complex and sodium.

(15)
A process for producing a compound represented by the Formula (IV):

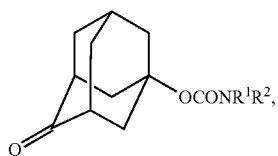

its salt, or a solvate thereof, wherein $R^1$ and $R^2$ are hydrogen, which comprises reacting 5-hydroxy-2-adamantanone and chlorosulfonyl isocyanate, followed by hydrolysis.

(16)
The process according to the above (6), wherein the process comprises a process according to any one of the above (10), (11), (11-1), or (12)-(15).

(17)
The process according to any one of the above (1)-(11), (11-1), (12)-(14) or (16), wherein $R^3$, $R^4$, $R^5$ and $R^6$ are hydrogen.

(18)
The process according to any one of the above (1)-(11), (11-1), or (12)-(17), wherein $R^1$ and $R^2$ are hydrogen.

(19)
A process for producing a compound represented by the Formula (VIII):

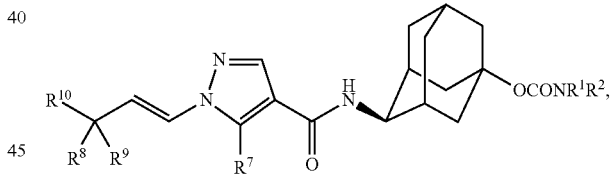

its salt, or a solvate thereof, wherein $R^1$ and $R^2$ are as defined in the above (1); $R^7$ is a group represented by the formula —Y—$R^{11}$, wherein Y is a single bond, —O— or —S—, and $R^{11}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^8$ and $R^9$ are each independently hydrogen, substituted or unsubstituted alkyl or halogen, or $R^8$ and $R^9$ taken together with the adjacent carbon atom to which they are attached may form a substituted or unsubstituted ring;

$R^{10}$ is
a group represented by the formula —C(=O)—$NR^{12}R^{13}$, wherein $R^{12}$ and $R^{13}$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl, or substituted or unsubstituted heterocyclylsulfonyl, or $R^{12}$ and $R^{13}$ taken together with the adjacent nitrogen atom to which they are attached may form a substituted or unsubstituted ring, or a group represented by the formula —$NR^{14}R^{15}$, wherein $R^{14}$ and $R^{15}$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl, or substituted or unsubstituted sulfamoyl, or $R^{14}$ and $R^{15}$ taken together with the adjacent nitrogen atom to which they are attached may form a substituted or unsubstituted ring;
which comprises obtaining a compound represented by the Formula (III):

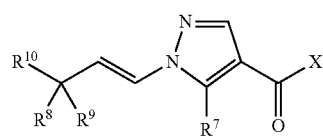

(III)

its salt, or a solvate thereof, wherein $R^1$ and $R^2$ are as defined in the above (1), by the process according to any one of the above (1)-(11), (11-1) and (12)-(18), followed by reacting the obtained compound represented by the Formula (III) and a compound represented by the Formula (VII):

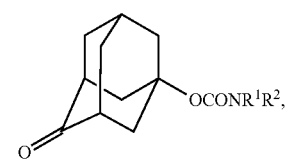

(VII)

wherein $R^7$, $R^8$, $R^9$ and $R^{10}$ are as defined above, X is hydroxy or a leaving group.
(20)
A compound represented by the Formula (IV):

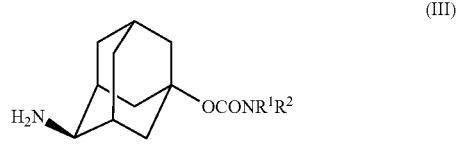

(IV)

its salt, or a solvate thereof, wherein $R^1$ and $R^2$ are each independently hydrogen, substituted or unsubstituted alkyl, or substituted or unsubstituted aryl.
(20-1)
The compound according to the above (20), its salt, or a solvate thereof, wherein $R^1$ and $R^2$ are hydrogen.

(20-2)
The crystal of a compound according to the above (20-1), its salt, or a solvate thereof, wherein the values of 2θ of the powder X-ray diffraction have two or more 2θ selected from 12.2±0.2, 16.8±0.2, 17.6±0.2, 19.0±0.2, 21.7±0.2, 24.5±0.2 and 34.2±0.2 degrees.
(21)
A compound represented by the Formula (VI):

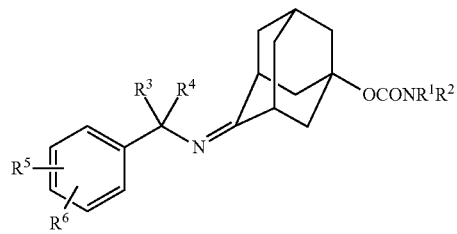

(VI)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, or substituted or unsubstituted alkyloxy, substituted or unsubstituted alkylsulfonyl, substituted or unsubstituted arylsulfonyl, or substituted or unsubstituted sulfamoyl.
(21-1)
The compound according to the above (21), its salt, or a solvate thereof, wherein $R^1$, $R^2$, $R^3$, $R^4$, $R^5$ and $R^6$ are hydrogen.
(22)
A compound represented by the Formula (II);

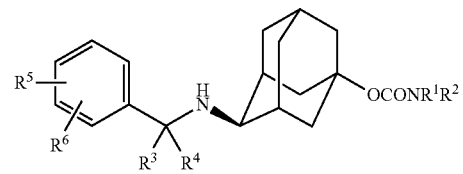

(II)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl.
(23)
Hydrochloride of the compound represented by the Formula (II) according to the above (22), or a solvate of the hydrochloride.
(23-1)
The crystal of Hydrochloride of a compound according to the above (23), or a solvate of the hydrochloride, wherein $R^1$, $R^2$, $R^3$, $R^4$, $R^5$ and $R^6$ are hydrogen, and the values of 2θ of the powder X-ray diffraction have two or more 2θ selected from 9.4±0.2, 15.6±0.2, 16.5±0.2, 18.9±0.2, 19.8±0.2, 21.1±0.2, 24.2±0.2, 26.5±0.2 and 28.6±0.2 degrees.

(24)
Benzoate of a compound represented by the Formula (II) according to the above (22), or toluene-solvated benzoate.

(24-1)
The crystal of the benzoate of the compound according to the above (24), or the toluene-solvated benzoate, wherein $R^1$, $R^2$, $R^3$, $R^4$, $R^5$ and $R^6$ are hydrogen, and the values of 2θ of the powder X-ray diffraction have two or more 2θ selected from 8.9±0.2, 10.1±0.2, 12.3±0.2, 15.2±0.2, 16.3±0.2, 18.0±0.2, 19.4±0.2, 19.7±0.2, 20.3±0.2, 26.1±0.2 and 26.4±0.2 degrees.

(25)
An acid addition salt of the compound represented by the Formula (III):

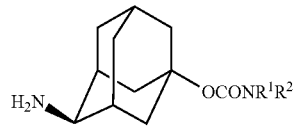

or a solvate of the acid addition salt, wherein $R^1$ and $R^2$ are each independently hydrogen, substituted or unsubstituted alkyl, or substituted or unsubstituted aryl.

(26)
A hydrochloride of the compound represented by the Formula (III) according to the above (25), or a dihydrate of the hydrochloride.

(26-1)
The hydrochloride of the compound according to the above (26), or the dihydrate of the hydrochloride, wherein $R^1$ and $R^2$ are hydrogen.

(26-2)
The Crystal of the hydrochloride of the compound according to the above (26-1), wherein the values of 2θ of the powder X-ray diffraction have two or more 2θ selected from 11.9±0.2, 14.9±0.2, 17.6±0.2, 18.4±0.2, 18.9±0.2, 19.8±0.2, 20.4±0.2, 23.2±0.2, 27.3±0.2, and 30.1±0.2 degrees.

(26-3)
The Crystal of the dihydrate of the hydrochloride of the compound according to the above (26-1), wherein the values of 2θ of the powder X-ray diffraction have two or more 2θ selected from 14.7±0.2, 18.9±0.2, 20.9±0.2, 25.6±0.2, 29.8±0.2, and 31.6±0.2 degrees.

Further, the present invention relates to the following.

(1A)
A process for producing an acid addition salt of a compound represented by the Formula (II):

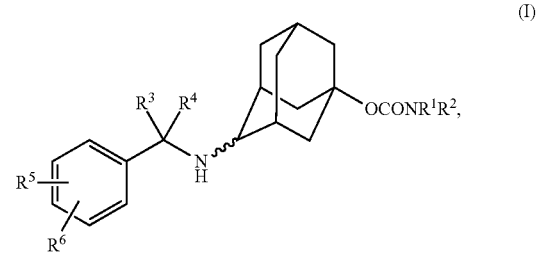

or a solvate of the acid addition salt, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl;

which comprises separating an acid addition salt of a compound represented by the Formula (II) or a solvate of the acid addition salt from a mixture in an acidic solvent of syn isomer and anti isomer of a compound represented by the Formula (I):

$$\text{(I)}$$

wherein $R^1$, $R^2$, $R^3$, $R^4$, $R^5$, and $R^6$ are as defined above.

(1A-1)
A process for producing an acid addition salt of a compound represented by the Formula (II):

$$\text{(II)}$$

or a solvate of the acid addition salt, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl;

which comprises precipitating an acid addition salt of a compound represented by the Formula (II) or a solvate of the acid addition salt, by adding an acid to a mixture of syn isomer and anti isomer of a compound represented by the Formula (I):

$$\text{(I)}$$

wherein $R^1$, $R^2$, $R^3$, $R^4$, $R^5$, and $R^6$ are as defined above, in the presence of a solvent.

(2A)

The process according to the above (1A) or (1A-1), wherein the process comprises crystallization.

(3A)

A process for producing a compound represented by the Formula (III):

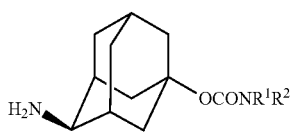

wherein $R^1$ and $R^2$ are as defined in the above (1A), its salt, or a solvate thereof, which comprises deprotecting an acid addition salt of a compound represented by the Formula (II):

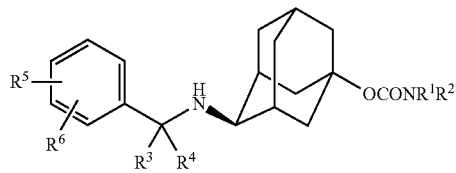

or a solvate of the acid addition salt, wherein $R^1$, $R^2$, $R^3$, $R^4$, $R^5$ and $R^6$ are as defined in the above (1A).

(4A)

The process according to the above (3A), wherein the deprotection is performed in the presence of an acid.

(5A)

The process according to the above (4A), wherein the acid is hydrochloric acid.

(6A)

The process for producing the compound represented by the Formula (III) according to the above (3A), its salt, or a solvate thereof, which comprises the process according to any one of the above (1A), (1A-1) and (2A).

(7A)

The process according to any one of the above (1A), (1A-1) and (2A)-(6A), wherein the acid addition salt is hydrochloride.

(8A)

The process according to any one of the above (1A), (1A-1) and (2A)-(6A), wherein the acid addition salt is benzoate.

(9A)

The process according to any one of the above (1A), (1A-1) and (2A)-(6A), wherein an acid addition salt of a compound represented by the Formula (II) or a solvate of the acid addition salt is a toluene-solvated benzoate.

(10A)

A process for producing a compound represented by the Formula the (VI):

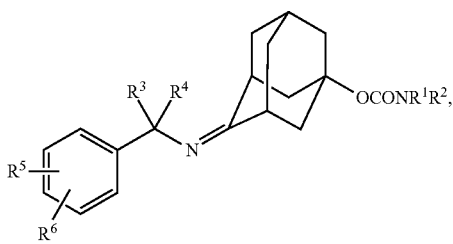

its salt, or a solvate thereof, wherein $R^1$, $R^2$, $R^3$, $R^4$, $R^5$ and $R^6$ are as defined in the above (1A) which comprises reacting a compound represented by the Formula (IV):

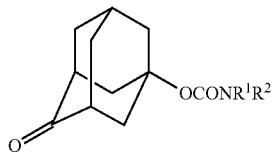

wherein $R^1$ and $R^2$ are as defined in the above (1A), and a compound represented by the Formula (V):

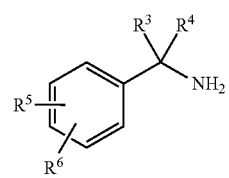

wherein $R^3$, $R^4$, $R^5$ and $R^6$ are as defined in the above (1A).

(11A)

A process for producing a compound represented by the Formula (I):

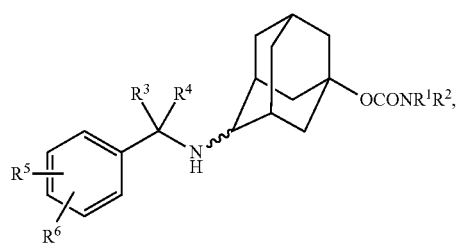

its salt, or a solvate thereof, wherein $R^1$, $R^2$, $R^3$, $R^4$, $R^5$ and $R^6$ are as defined in the above (1A), which comprises reducing a compound represented by the Formula (VI):

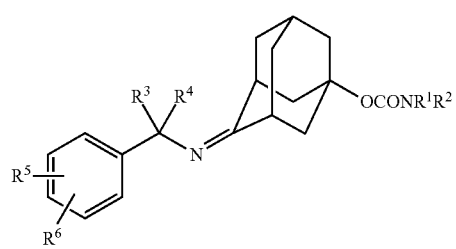

wherein $R^1$, $R^2$, $R^3$, $R^4$, $R^5$ and $R^6$ are as defined in the above (1A).

(12A)

The process according to the above (10A) or (11A), wherein the process comprises adding an acid.

(13A)

The process according to the above (11A) or (12A), wherein a hydride reducing agent is used for reducing.

(14A)

The process according to the above (11A) or (12A), wherein the process comprises reduction using one or more reducing agent(s) selected from sodium tri(acetoxy)hydroborate, sodium borohydride, lithium tetrahydroborate, pyridine borane complex, tetrahydrofuran borane complex, dimethyl sulfide borane complex, 2-picoline borane complex and sodium.

(15A)

A process for producing a compound represented by the Formula (IV):

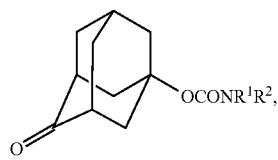

its salt, or a solvate thereof, wherein $R^1$ and $R^2$ are hydrogen, which comprises reacting 5-hydroxy-2-adamantanone and chlorosulfonyl isocyanate, followed by hydrolysis.

(16A)

The process according to the above (6A), wherein the process comprises a process according to any one of the above (10A) to (15A).

(17A)

The process according to any one of the above (1A), (1A-1), (2A)-(14A) and (16A), wherein $R^3$, $R^4$, $R^5$ and $R^6$ are hydrogen.

(18A)

The process according to any one of the above (1A), (1A-1) and (2A)-(17A), wherein $R^1$ and $R^2$ are hydrogen.

(19A)

A process for producing a compound represented by the Formula (VIII):

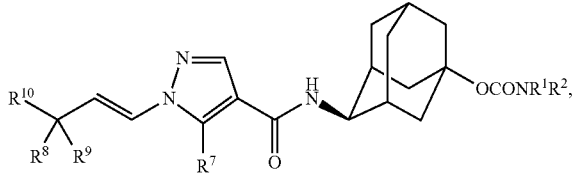

its salt, or a solvate thereof, wherein $R^1$ and $R^2$ are as defined in the above (1A); $R^7$ is a group represented by the formula —Y—$R^{11}$, wherein Y is a single bond, —O— or —S—, and $R^{11}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^8$ and $R^9$ are each independently hydrogen, substituted or unsubstituted alkyl or halogen, or $R^8$ and $R^9$ taken together with the adjacent carbon atom to which they are attached may form a substituted or unsubstituted ring;
$R^{10}$ is
a group represented by the formula —C(=O)—$NR^{12}R^{13}$, wherein $R^{12}$ and $R^{13}$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl, or substituted or unsubstituted heterocyclylsulfonyl, or $R^{12}$ and $R^{13}$ taken together with the adjacent nitrogen atom to which they are attached may form a substituted or unsubstituted ring, or a group represented by the formula —$NR^{14}R^{15}$, wherein $R^{14}$ and $R^{15}$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl, or substituted or unsubstituted sulfamoyl, or $R^{14}$ and $R^{15}$ taken together with the adjacent nitrogen atom to which they are attached may form a substituted or unsubstituted ring;
which comprises obtaining a compound represented by the Formula (III);

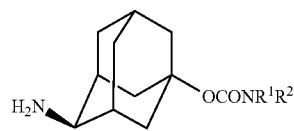

its salt, or a solvate thereof, wherein $R^1$ and $R^2$ are as defined in the above (1A), by the process according to any one of the above (1A), (1A-1) and (2A)-(18A), followed by reacting the obtained compound represented by the Formula (III) and a compound represented by the Formula (VII):

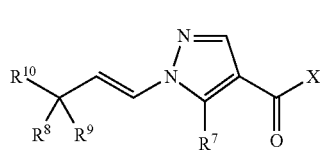

wherein $R^7$, $R^8$, $R^9$ and $R^{10}$ are as defined above, X is hydroxy or a leaving group.

(20A)

A compound represented by the Formula (IV):

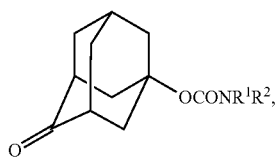

its salt, or a solvate thereof, wherein $R^1$ and $R^2$ are each independently hydrogen, substituted or unsubstituted alkyl, or substituted or unsubstituted aryl.

(20A-1)

The compound according to the above (20A), its salt, or a solvate thereof, wherein $R^1$ and $R^2$ are hydrogen.

(20A-2)

The crystal of a compound according to the above (20A-1), its salt, or a solvate thereof, wherein the values of 2θ of the powder X-ray diffraction have two or more 2θ selected from 12.2±0.2, 16.8±0.2, 17.6±0.2, 19.0±0.2, 21.7±0.2, 24.5±0.2 and 34.2±0.2 degrees.

(21A)

A compound represented by the Formula (VI):

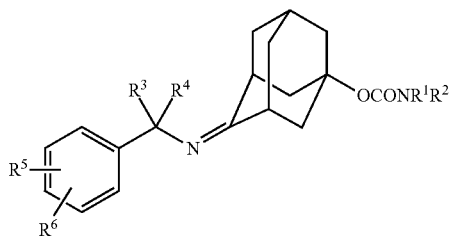

(VI)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, or substituted or unsubstituted alkyloxy, substituted or unsubstituted alkylsulfonyl, substituted or unsubstituted arylsulfonyl, or substituted or unsubstituted sulfamoyl.

(21A-1)

The compound according to the above (21A), its salt, or a solvate thereof, wherein $R^1$, $R^2$, $R^3$, $R^4$, $R^5$ and $R^6$ are hydrogen.

(22A)

A compound represented by the Formula (II):

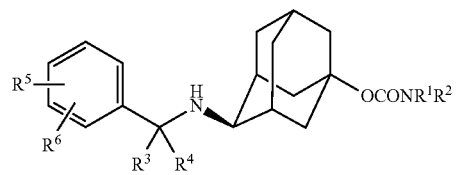

(II)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl.

(23A)

Hydrochloride of the compound represented by the Formula (II) according to the above (22A), or a solvate of the hydrochloride.

(23A-1)

The crystal of Hydrochloride of a compound according to the above (23A), or a solvate of the hydrochloride, wherein $R^1$, $R^2$, $R^3$, $R^4$, $R^5$ and $R^6$ are hydrogen, and the values of 2θ of the powder X-ray diffraction have two or more 2θ selected from 9.4±0.2, 15.6±0.2, 16.5±0.2, 18.9±0.2, 19.8±0.2, 21.1±0.2, 24.2±0.2, 26.5±0.2 and 28.6±0.2 degrees.

(24A)

Benzoate of a compound represented by the Formula (II) according to the above (22A), or toluene-solvated benzoate.

(24A-1)

The crystal of the benzoate of the compound according to the above (24A), or the toluene-solvated benzoate, wherein $R^1$, $R^2$, $R^3$, $R^4$, $R^5$ and $R^6$ are hydrogen, and the values of 2θ of the powder X-ray diffraction have two or more 2θ selected from 8.9±0.2, 10.1±0.2, 12.3±0.2, 15.2±0.2, 16.3±0.2, 18.0±0.2, 19.4±0.2, 19.7±0.2, 20.3±0.2, 26.1±0.2 and 26.4±0.2 degrees.

(25A)

An acid addition salt of the compound represented by the Formula (III):

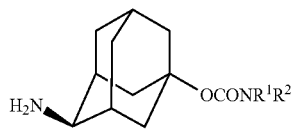

(III)

or a solvate of the acid addition salt, wherein $R^1$ and $R^2$ are each independently hydrogen, substituted or unsubstituted alkyl, or substituted or unsubstituted aryl.

(25A-1)

The acid addition salt of the compound according to the above (25A) or the solvate of the acid addition salt, wherein $R^1$ and $R^2$ are hydrogen.

(25A-2)

The crystal of hydrochloride of the compound according to the above (25A-1) stated above or of a solvate of the hydrochloride, wherein the values of 2θ of the powder X-ray diffraction have two or more 2θ selected from 11.9±0.2, 14.9±0.2, 17.6±0.2, 18.4±0.2, 18.9±0.2, 19.8±0.2, 20.4±0.2, 23.2±0.2, 27.3±0.2, and 30.1±0.2 degrees.

(1B)

A process for producing an acid addition salt of a compound represented by the Formula (II):

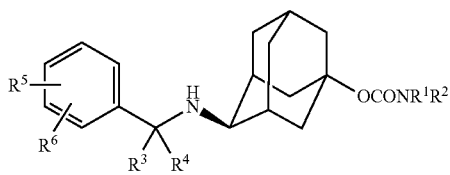

(II)

or a solvate of the acid addition salt, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl;

which comprises separating an acid addition salt of a compound represented by the Formula (II) or a solvate of the acid addition salt from a mixture in an acidic solvent of syn isomer and anti isomer of a compound represented by the Formula (I):

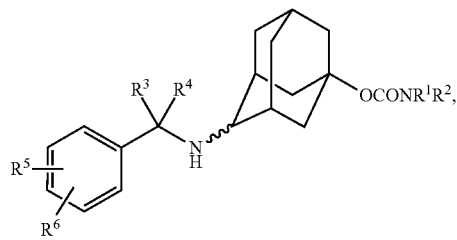

wherein $R^1$, $R^2$, $R^3$, $R^4$, $R^5$, and $R^6$ are as defined above.
(2B)
The process according to the above (1B), wherein the process comprises crystallization.
(3B)
A process for producing a compound represented by the Formula (III):

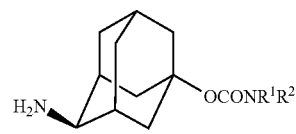

wherein $R^1$ and $R^2$ are as defined in the above (1B), its salt, or a solvate thereof, which comprises deprotecting an acid addition salt of a compound represented by the Formula (II):

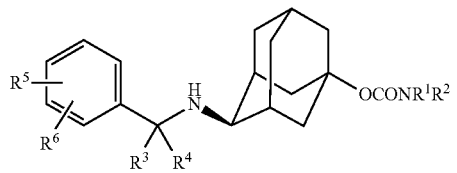

or a solvate of the acid addition salt, wherein $R^1$, $R^2$, $R^3$, $R^4$, $R^5$ and $R^6$ are as defined in the above (1B).
(4B)
The process for producing the compound represented by the Formula (III) according to the above (3B), its salt, or a solvate thereof, which comprises the process according to the above (1B) or (2B).
(5B)
A process for producing a compound represented by the Formula the (VI):

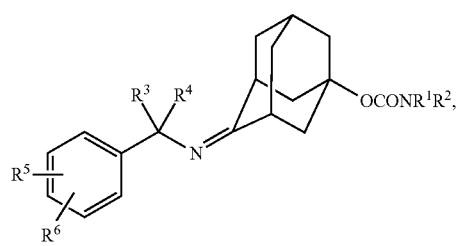

its salt, or a solvate thereof, wherein $R^1$, $R^2$, $R^3$, $R^4$, $R^5$ and $R^6$ are as defined in the above (1B) which comprises reacting a compound represented by the Formula (IV):

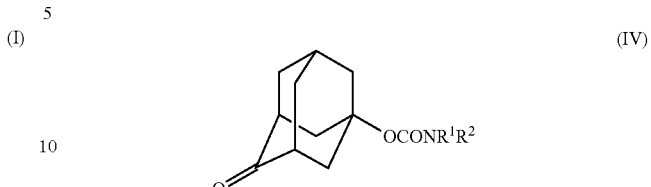

wherein $R^1$ and $R^2$ are as defined in the above (1B), and a compound represented by the Formula (V):

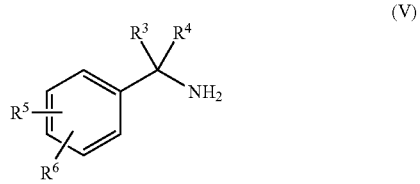

wherein $R^3$, $R^4$, $R^5$ and $R^6$ are as defined in the above (1B).
(6B)
A process for producing a compound represented by the Formula (I):

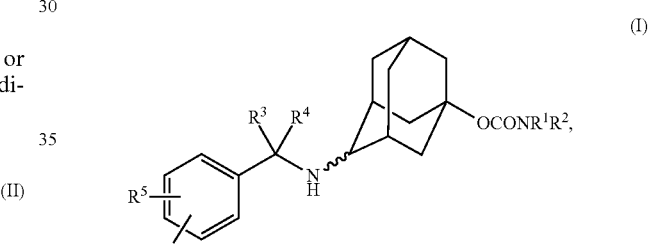

its salt, or a solvate thereof, wherein $R^1$, $R^2$, $R^3$, $R^4$, $R^5$ and $R^6$ are as defined in the above (1B), which comprises reducing a compound represented by the Formula (VI):

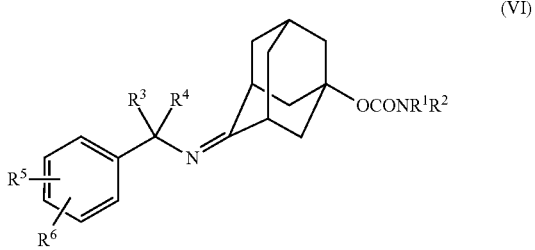

wherein $R^1$, $R^2$, $R^3$, $R^4$, $R^5$ and $R^6$ are as defined in the above (1B).
(7B)
The process according to the above (5B) or (6B), wherein the process comprises adding an acid.
(8B)
The process according to the above (6B) or (7B), wherein a hydride reducing agent is used for reducing.
(9B)
The process according to the above (6B) or (7B), wherein the process comprises reduction using one or more reducing agent(s) selected from sodium tri(acetoxy)hydroborate, sodium borohydride, lithium tetrahydroborate, pyridine borane complex, tetrahydrofuran borane complex, dimethyl sulfide borane complex, 2-picoline borane complex and sodium.

(10B)

A process for producing a compound represented by the Formula (IV):

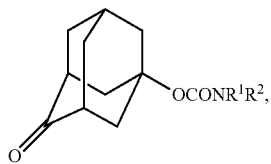

its salt, or a solvate thereof, wherein $R^1$ and $R^2$ are hydrogen, which comprises reacting 5-hydroxy-2-adamantanone and chlorosulfonyl isocyanate, followed by hydrolysis.

(11B)

The process according to the above (4B), wherein the process comprises a process according to any one of the above (5B) to (10B).

(12B)

The process according to any one of the above (1B)-(9B) and (11B), wherein $R^3$, $R^4$, $R^5$ and $R^6$ are hydrogen.

(13B)

The process according to any one of the above (1B) to (12B), wherein $R^1$ and $R^2$ are hydrogen.

(14B)

A process for producing a compound represented by the Formula (VIII):

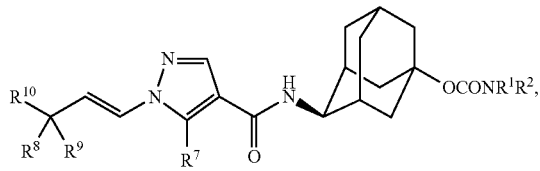

its salt, or a solvate thereof, wherein $R^1$ and $R^2$ are as defined in the above (1B); $R^7$ is a group represented by the formula —Y—$R^{11}$, wherein Y is a single bond, —O— or —S—, and $R^{11}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^8$ and $R^9$ are each independently hydrogen, substituted or unsubstituted alkyl or halogen, or $R^8$ and $R^9$ taken together with the adjacent carbon atom to which they are attached may form a substituted or unsubstituted ring;

$R^{10}$ is a group represented by the formula —C(=O)—$NR^{12}R^{13}$, wherein $R^{12}$ and $R^{13}$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl, or substituted or unsubstituted heterocyclylsulfonyl, or $R^{12}$ and $R^{13}$ taken together with the adjacent nitrogen atom to which they are attached may form a substituted or unsubstituted ring, or a group represented by the formula —$NR^{14}R^{15}$, wherein $R^{14}$ and $R^{15}$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl, or substituted or unsubstituted sulfamoyl, or $R^{14}$ and $R^{15}$ taken together with the adjacent nitrogen atom to which they are attached may form a substituted or unsubstituted ring;

which comprises obtaining a compound represented by the Formula (III):

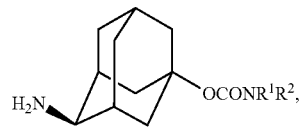

its salt, or a solvate thereof, wherein $R^1$ and $R^2$ are as defined in the above (1B), by the process according to any one of the above (1B) to (13B), followed by reacting the obtained compound represented by the Formula (III) and a compound represented by the Formula (VII):

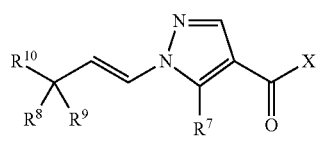

wherein $R^7$, $R^8$, $R^9$ and $R^{10}$ are as defined above, X is hydroxy or a leaving group.

(15B)

A compound represented by the Formula (IV):

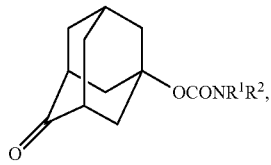

its salt, or a solvate thereof, wherein $R^1$ and $R^2$ are each independently hydrogen, substituted or unsubstituted alkyl, or substituted or unsubstituted aryl.

(16B)

A compound represented by the Formula (VI):

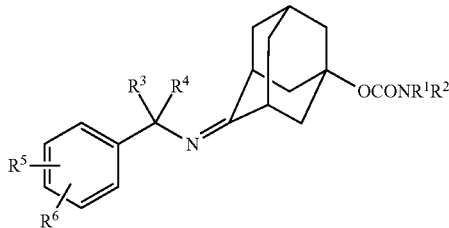

(VI)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, or substituted or unsubstituted alkyloxy, substituted or unsubstituted alkylsulfonyl, substituted or unsubstituted arylsulfonyl, or substituted or unsubstituted sulfamoyl.

(17B)

A compound represented by the Formula (II):

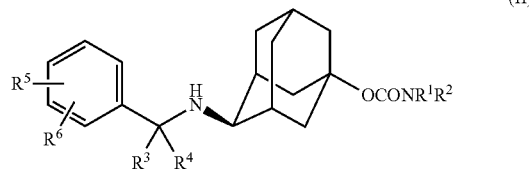

(II)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl.

For purposes of this description, reacting a compound with a compound includes reacting a compound, its salt, or a solvate thereof with a compound, its salt, or a solvate thereof.

Effect of the Invention

The novel process for producing a compound represented by the Formula (III) of the present invention, its salt, or a solvate thereof can be applied in industrial production as a process providing high yield and safety.

Moreover, a compound represented by the Formula (III), its salt, or a solvate thereof is a useful compound as synthetic raw material or an intermediate for pharmaceuticals or the like. By using a compound represented by the Formula (III), its salt, or a solvate thereof, a compound represented by the Formula (VIII), its salt, or a solvate thereof can be efficiently produced.

MODE FOR CARRYING OUT THE INVENTION

Figure 1:
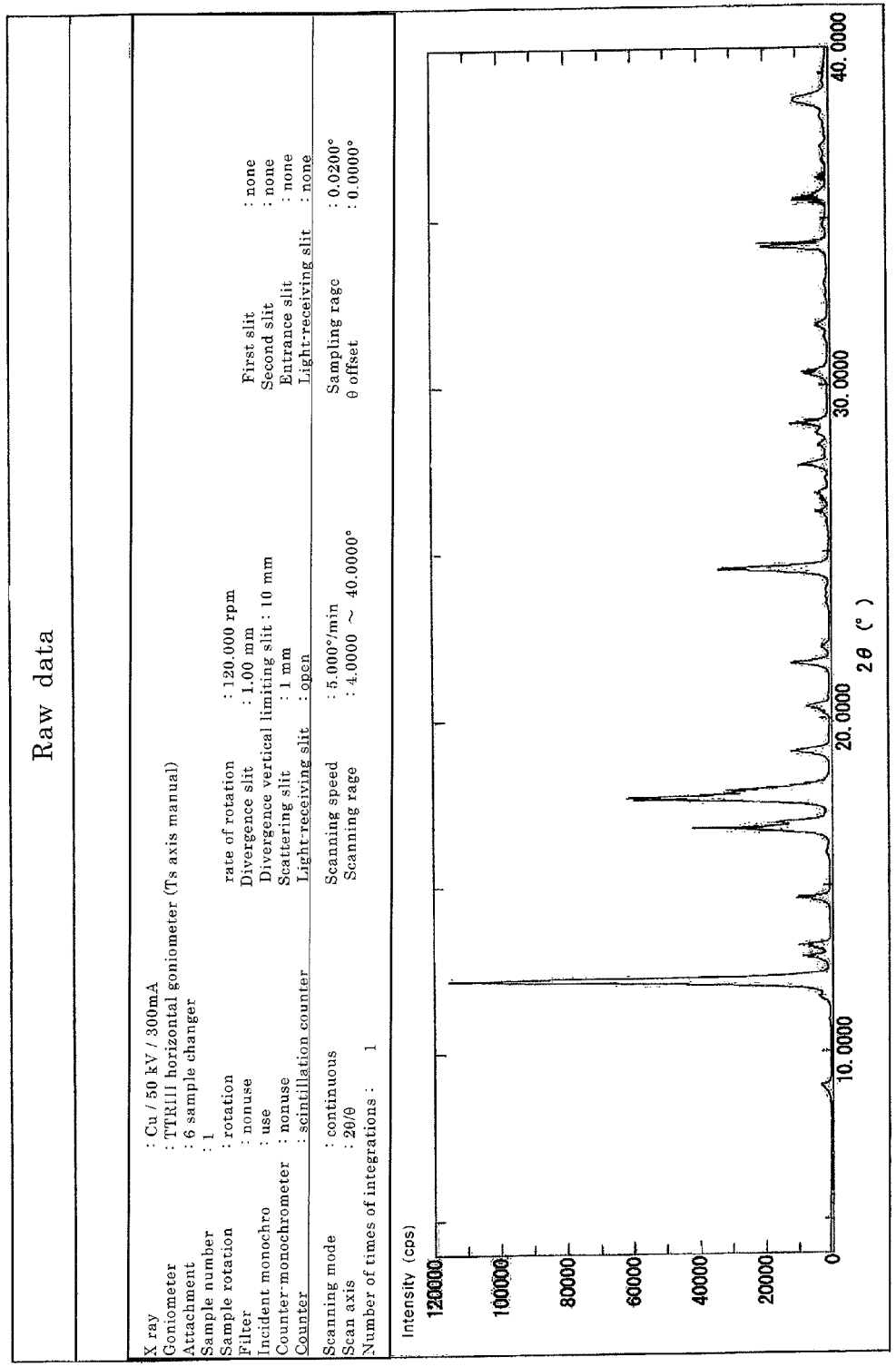
FIG. 1 shows data of powder X-ray diffraction for compound (IV-1).

In the following, meanings of terms used in the present specification will be explained. Each term has the same meaning when used alone or in combination with other term in this description.

"Halogen" includes fluorine, chlorine, bromine or iodine.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like. Furthermore, "Alkynyl" may have a double bond.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, spiro hydrocarbon group or the like. Preferable is cyclopropyl, cyclobutyl, cyclopentyl, cyclohexyl or bridged cyclic hydrocarbon group.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group which is derived by excluding one hydrogen from a cycle which consists of two hydrocarbon rings that share one carbon atom. Example includes spiro[3.4]octyl or the like.

"Cycloalkenyl" means C3 to C10 cyclic unsaturated aliphatic hydrocarbon group, and example includes cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl or 3-cyclopenten-1-yl), cyclohexenyl (e.g.: 1-cyclohexen-1-yl, 2-cyclohexen-1-yl or 3-cyclohexen-1-yl), cycloheptenyl (e.g.: 1-cycloheptenyl), cyclooctenyl (e.g.: 1-cyclooctenyl) or the like. Preferable is cyclopropenyl, cyclobutenyl, cyclopentenyl or cyclohexenyl. Cycloalkenyl also includes bridged cyclic hydrocarbon group and spiro hydrocarbon group which have an unsaturated bond in the ring.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group or a fused aromatic heterocyclic group. The monocyclic aromatic heterocyclic group means a group derived from a 5- to 8-membered aromatic ring which may contain 1 to 4 oxygen, sulfur and/or nitrogen atom(s) in the ring, and may have a bond at a substitutable arbitrary position.

The fused aromatic heterocyclic group means a group in which a 5- to 8-membered aromatic ring optionally containing 1 to 4 oxygen, sulfur and/or nitrogen atom(s) in the ring is fused with 1 to 4 of 5- to 8-membered aromatic carbocycle(s) or other 5- to 8-membered aromatic heterocycle(s), and which may have a bond at a substitutable arbitrary position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), dibenzofuryl, benzoxazolyl, benzothiazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8 cinnolinyl), quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocyclyl" means a nonaromatic heterocyclic group which contains at least one nitrogen, oxygen or sulfur atom(s) in the ring, and may have a bond at a substitutable arbitrary position. Moreover, the nonaromatic heterocyclic group can be bridged with a C1 to C4 alkyl chain, or can be fused with cycloalkane (5- to 6-membered ring is preferable) or benzene ring. "Nonaromatic heterocyclic group" can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl or the like.

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl.

The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl" and the heterocyclyl part of "heterocyclylcarbonyl" respectively mean the above "alkyl", the above "alkenyl", the above "cycloalkyl", the above "cycloalkenyl", the above "aryl", the above "heteroaryl" and the above "heterocyclyl".

The alkyl part of "alkyloxy", "alkylsulfonyl" and "alkyloxycarbonyl" means the above "alkyl".

The aryl part of "arylsulfonyl" means the above "aryl".

The heteroaryl part of "heteroarylsulfonyl" means the above "heteroaryl".

The heterocyclyl part of "heterocyclylsulfonyl" means the above "heterocyclyl".

"Substituted alkyl", "substituted aryl", "substituted alkyloxy", "substituted alkylsulfonyl", "substituted arylsulfonyl", "substituted sulfamoyl", "substituted alkenyl", "substituted alkynyl", "substituted heteroaryl", "substituted cycloalkyl", "substituted cycloalkenyl", "substituted heterocyclyl", "a ring formed by taking together $R^8$ and $R^9$ with the adjacent carbon atom to which they are attached", "substituted heteroarylsulfonyl", "substituted heterocyclylsulfonyl", "a ring formed by taking together $R^{12}$ and $R^{13}$ with the adjacent nitrogen atom to which they are attached", "substituted acyl", "substituted carbamoyl", "substituted thiocarbamoyl", "substituted alkyloxycarbonyl" or "a ring formed by taking together $R^{14}$ and $R^{15}$ with the adjacent nitrogen atom to which they are attached" may be substituted with 1 to 4 substituent(s) selected from a group consisting of, for example, halogen, hydroxy, carboxy, nitro, cyano;

substituted or unsubstituted alkyl (as a substituent, halogen, hydroxy, carboxy, cyano, substituted or unsubstituted amino, alkyl, aryl, cycloalkyl, heteroaryl, heterocyclyl, alkyloxy, alkyloxycarbonyl, alkyloxycarbonylamino or carbamoyl, e.g. methyl, ethyl, isopropyl, tert-butyl, $CF_3$, $CH_2OH$, $CH_2CH_2OH$, $CH_2COOCH_3$, $CH_2NH_2$, $CH_2CN$ or benzyl);

substituted or unsubstituted alkenyl (as a substituent, halogen, carboxy, alkyl, aryl, cycloalkyl, heteroaryl or heterocyclyl, e.g. vinyl);

substituted or unsubstituted alkynyl (as a substituent, halogen, alkyl, aryl, cycloalkyl, heteroaryl or heterocyclyl, e.g. ethynyl);

substituted or unsubstituted aryl (as a substituent, halogen, hydroxy, cyano, substituted or unsubstituted amino, substituted or unsubstituted alkyl, aryl, cycloalkyl, heteroaryl, heterocyclyl, substituted or unsubstituted alkyloxy, cycloalkyloxy, substituted or unsubstituted heterocyclyloxy or alkyloxycarbonyl, e.g. phenyl, naphthyl);

substituted or unsubstituted cycloalkyl (as a substituent, halogen, cyano, alkyl, aryl, cycloalkyl, heteroaryl, heterocyclyl or alkyloxycarbonyl, e.g. cyclopropyl, cyclobutyl);

substituted or unsubstituted cycloalkenyl (as a substituent, halogen, alkyl, aryl, cycloalkyl, heteroaryl, heterocyclyl, e.g. cyclopropenyl);

substituted or unsubstituted heteroaryl (as a substituent, halogen, alkyl, aryl, cycloalkyl, heteroaryl, heterocyclyl or substituted or unsubstituted alkyloxy, e.g. tetrazolyl, indolyl, pyrazolyl);

substituted or unsubstituted heterocyclyl (as a substituent, halogen, alkyl, aryl, cycloalkyl, heteroaryl, heterocyclyl or alkylsulfonyl, e.g. pyrrolidinyl, morpholinyl, piperazinyl, piperidyl);

substituted or unsubstituted alkyloxy (as a substituent, halogen, carboxy, cyano, alkyl, aryl, cycloalkyl, heteroaryl or heterocyclyl, e.g. methoxy, ethoxy, propoxy, butoxy, $OCF_3$);

substituted or unsubstituted aryloxy (as a substituent, halogen, alkyl, aryl, cycloalkyl, heteroaryl or heterocyclyl, e.g. phenyloxy);

substituted or unsubstituted silyloxy;

substituted or unsubstituted amino (e.g. alkylamino (e.g. methylamino, ethylamino, dimethylamino), acylamino (e.g. acetylamino, benzoylamino), arylalkylamino (e.g. benzylamino, tritylamino), hydroxyamino, alkylaminoalkyl (e.g. diethylaminomethyl), alkyloxycarbonylamino, alkylsulfonylamino, carbamoylamino, heterocyclylcarbonylamino, arylsulfonylamino or heteroarylsulfonylamino);

substituted or unsubstituted carbamoyl (as a substituent, hydroxy, cyano, substituted or unsubstituted alkyl, alkyloxy or alkylsulfonyl, e.g. alkylcarbamoyl (e.g. methylcarbamoyl, ethylcarbamoyl, dimethylcarbamoyl, phenylethylcarbamoyl, dimethylaminoethylcarbamoyl, isopropylcarbamoyl, hydroxyethylcarbamoyl), alkylsulfonylcarbamoyl, heteroarylalkylcarbamoyl, substituted or unsubstituted alkyloxycarbamoyl);

substituted or unsubstituted carbamoyloxy (as a substituent, halogen, alkyl, aryl, cycloalkyl, heteroaryl or heterocyclyl);

substituted or unsubstituted acyl (as a substituent, halogen, alkyl, aryl, cycloalkyl, heteroaryl or heterocyclyl, e.g. alkylcarbonyl, arylcarbonyl, heteroarylcarbonyl, heterocyclylcarbonyl, formyl, acetyl);

substituted or unsubstituted alkylsulfonyl (as a substituent, halogen, alkyl, aryl, cycloalkyl, heteroaryl or heterocyclyl, e.g. methanesulfonyl, ethanesulfonyl);

substituted or unsubstituted arylsulfonyl;

substituted or unsubstituted heteroarylsulfonyl (as a substituent, halogen, alkyl, aryl, cycloalkyl, heteroaryl or heterocyclyl);

substituted or unsubstituted sulfamoyl;

substituted or unsubstituted alkyloxycarbonyl (as a substituent, halogen, alkyl, aryl, cycloalkyl, heteroaryl or heterocyclyl, e.g. methoxycarbonyl, ethoxycarbonyl, tert-butoxycarbonyl);

aryloxycarbonyl;

heteroaryloxycarbonyl;

heterocyclyloxycarbonyl;

cycloalkylsulfonyl;

heteroarylsulfonyl;

heterocyclylsulfonyl; alkylsulfinyl; cycloalkylsulfinyl; arylsulfinyl; heteroarylsulfinyl;

heterocyclylsulfinyl;

nitroso;

alkenyloxy (e.g. vinyloxy, allyloxy);

arylalkyloxy (e.g. benzyloxy);

azido;

isocyano; isocyanato; thiocyanato; isothiocyanato; mercapto; alkylthio (e.g. methylthio);

formyloxy; haloformyl; oxalo; thioformyl; thiocarboxy; dithiocarboxy; thiocarbamoyl; sulfino; sulfo; sulfoamino; hydrazine; ureido; amidino; guanidino; phthalimido; oxo and the like.

Example of a substituent of "substituted sulfamoyl", "substituted amino", "substituted carbamoyl" or "substituted thiocarbamoy" includes alkyl; alkenyl;

substituted or unsubstituted aryl (as a substituent, carboxy, alkyloxy or sulfamoyl); heteroaryl; alkylcarbonyl; arylcarbonyl; heteroarylcarbonyl; heterocyclylcarbonyl; alkyloxycarbonyl; aryloxycarbonyl; heteroaryloxycarbonyl; heterocyclyloxycarbonyl; sulfamoyl; alkylsulfonyl; carbamoyl; cycloalkylsulfonyl; arylsulfonyl; heteroarylsulfonyl; heterocyclylsulfonyl; acyl; hydroxy; alkylsulfinyl; cycloalkylsulfinyl; arylsulfinyl; heteroarylsulfinyl; heterocyclylsulfinyl, amino or the like.

The alkyl part of "alkyloxycarbonylamino", "alkylamino", "arylalkylamino", "alkylaminoalkyl", "alkylsulfonylamino", "alkylcarbamoyl", "alkylsulfonylcarbamoyl", "heteroarylalkylcarbamoyl", "alkyloxycarbamoyl", "alkylsulfinyl", "arylalkyloxy" and "alkylthio" means the above "alkyl".

The alkenyl part of "alkenyloxy" means the above "alkenyl".

The cycloalkyl part of "cycloalkyloxy", "cycloalkylsulfonyl" and "cycloalkylsulfinyl" means the above "cycloalkyl".

The aryl part of "aryloxy", "arylalkylamino", "arylsulfonylamino", "aryloxycarbonyl", "arylsulfinyl" and "arylalkyloxy" means the above "aryl".

The heteroaryl part of "heteroarylsulfonylamino", "heteroarylalkylcarbamoyl", "heteroaryloxycarbonyl" and "heteroarylsulfinyl" means the above "heteroaryl".

The heterocyclyl part of "heterocyclyloxy", "heterocyclylcarbonylamino", "heterocyclyloxycarbonyl" and "heterocyclylsulfinyl" means the above "heterocyclyl."

Among the compounds of the present invention, compounds of the following embodiments are preferable.

$R^1$ and $R^2$ are each independently hydrogen, substituted or unsubstituted alkyl, or substituted or unsubstituted aryl.

Preferably, $R^1$ and $R^2$ are each independently hydrogen or substituted or unsubstituted alkyl. More preferable is hydrogen.

$R^3$ and $R^4$ are each independently hydrogen, substituted or unsubstituted alkyl, or substituted or unsubstituted aryl.

Preferably, $R^3$ and $R^4$ are each independently hydrogen, or substituted or unsubstituted alkyl. More preferable is hydrogen.

$R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl or substituted or unsubstituted sulfamoyl.

Preferable is hydrogen.

Among the compounds of the present invention, compounds represented by the Formula (V) are preferably of the following embodiments.

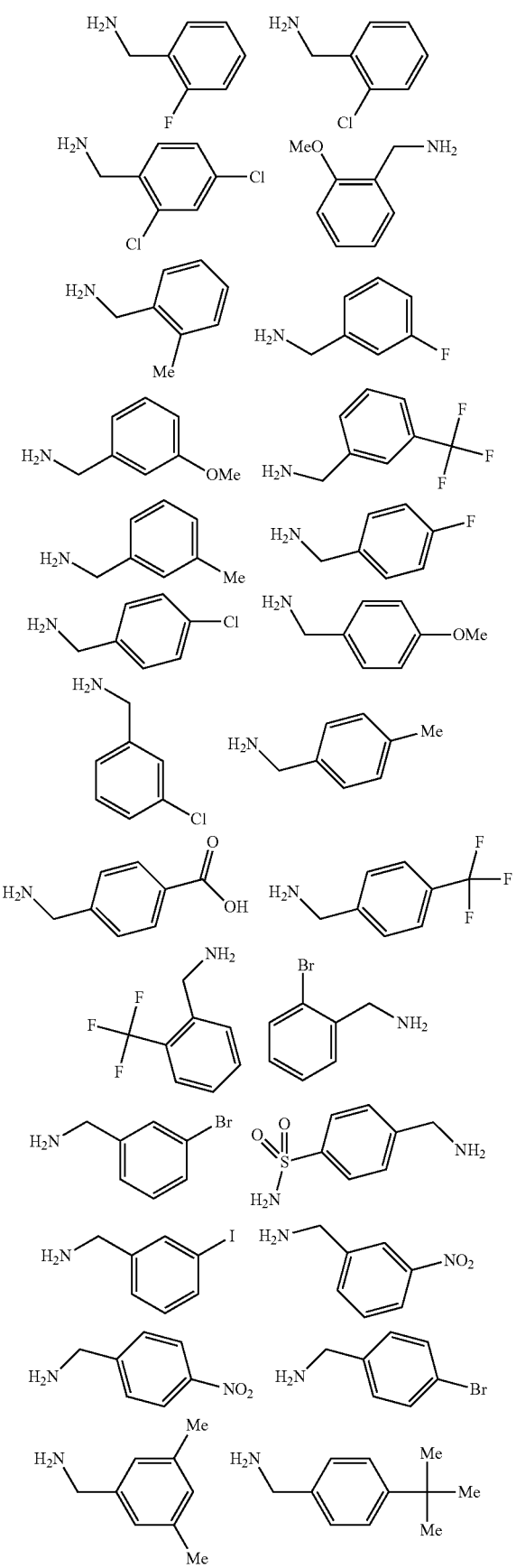
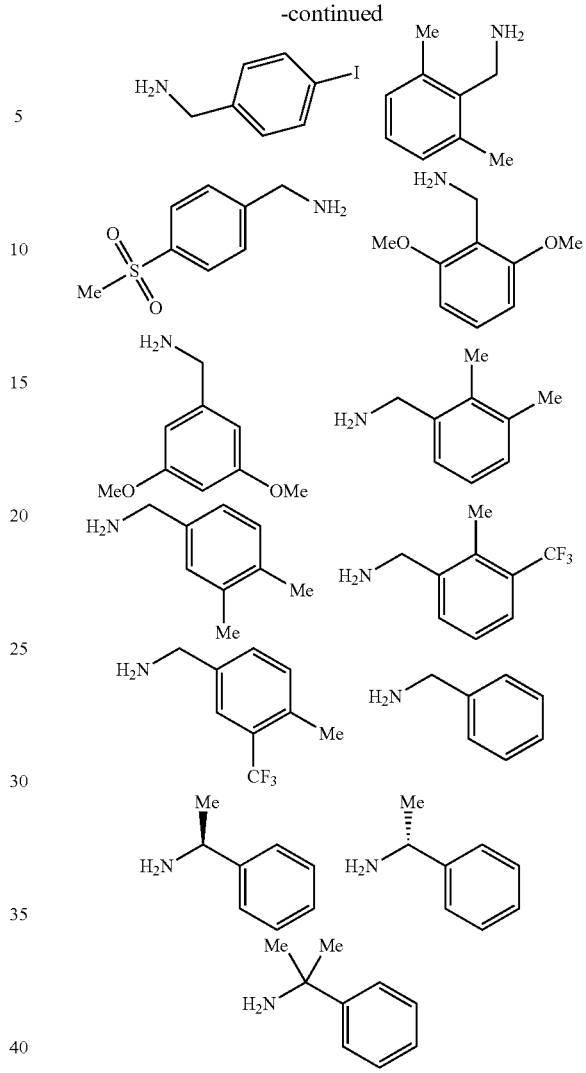

Particularly preferable is as follows;

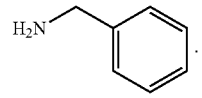

$R^7$ is a group represented by the Formula —Y—$R^{11}$.

Y is a single bond, —O— or —S—, preferably —O— or —S—, and more preferably —O—.

$R^{11}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocyclyl.

Preferable is substituted or unsubstituted alkyl.

$R^8$ and $R^9$ are each independently hydrogen, substituted or unsubstituted alkyl or halogen, or $R^8$ and $R^9$ taken together with the adjacent carbon atom to which they are attached may form a substituted or unsubstituted ring.

Preferably, $R^8$ and $R^9$ are each independently hydrogen, substituted or unsubstituted alkyl or halogen. More preferable is substituted or unsubstituted alkyl.

"A ring formed by taking together $R^8$ and $R^9$ with the adjacent carbon atom to which they are attached" means a 3- to 15-membered saturated or unsaturated hydrocarbon ring or a 3- to 15-membered saturated or unsaturated hetero ring containing 1 to 4 oxygen, sulfur, and/or nitrogen atom(s) in said hydrocarbon ring. Preferable is nonaromatic ring, example includes cyclopropane, cyclobutane, cyclopentane, cyclohexane, cycloheptane, cyclooctane, cyclopropene, cyclobutene, cyclopentene, cyclohexene, cycloheptene, a saturated or unsaturated hetero ring containing 1 to 4 oxygen, sulfur, and/or nitrogen atom(s) in the above hydrocarbon ring.

For example, as a group of the formula: $—C(R^8R^9)—$, wherein $R^8$ and $R^9$ taken together with the adjacent carbon atom to which they are attached form a ring, the following groups are exemplified. Any position that can be substituted in each of the rings may be substituted.

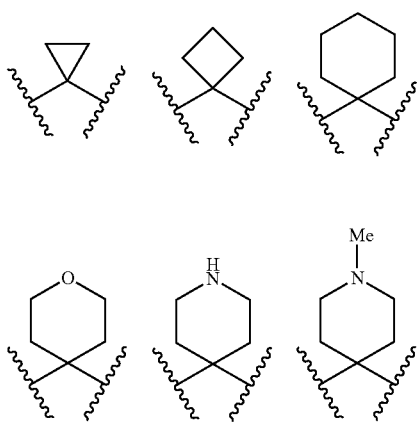

$R^{10}$ is a group represented by the formula: $—C(=O)—NR^{12}R^{13}$, or a group represented by the formula: $—NR^{14}R^{15}$.

Preferable is a group represented by the formula: $—NR^{14}R^{15}$.

$R^{12}$ and $R^{13}$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl, or substituted or unsubstituted heterocyclylsulfonyl, or $R^{12}$ and $R^{13}$ taken together with the adjacent nitrogen atom to which they are attached may form a substituted or unsubstituted ring.

Preferably, $R^{12}$ and $R^{13}$ are each independently hydrogen, or substituted or unsubstituted alkyl.

$R^{14}$ and $R^{15}$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl, or substituted or unsubstituted sulfamoyl, or $R^{14}$ and $R^{15}$ taken together with the adjacent nitrogen atom to which they are attached may form a substituted or unsubstituted ring.

Preferably, $R^{14}$ and $R^{15}$ are each independently hydrogen, substituted or unsubstituted alkyl, substituted or unsubstituted acyl, substituted or unsubstituted alkylsulfonyl, or substituted or unsubstituted alkyloxycarbonyl.

More preferably, $R^{14}$ and $R^{15}$ are each independently hydrogen or substituted or unsubstituted acyl.

"A ring formed by taking together $R^{12}$ and $R^{13}$ with the adjacent nitrogen atom to which they are attached" and "a ring formed by taking together $R^{14}$ and $R^{15}$ with the adjacent nitrogen atom to which they are attached" mean 3- to 15-membered nonaromatic hetero ring which may contain 1 to 4 oxygen, sulfur, and/or nitrogen atom(s) besides the above nitrogen atom in the ring. Moreover, the nonaromatic hetero ring can be bridged with a C1 to C4 alkyl chain, or can be fused with cycloalkane (5- to 6-membered ring is preferable) or benzene ring. The ring can be saturated or unsaturated as long as it is nonaromatic. Preferable is a 5- to 8-membered ring. For example, as a group of the formula: $—NR^{12}R^{13}$, wherein $R^{12}$ and $R^{13}$ taken together with the adjacent nitrogen atom to which they are attached form a ring and a group of the formula: $—NR^{14}R^{15}$, wherein $R^{14}$ and $R^{15}$ taken together with the adjacent nitrogen atom to which they are attached form a ring, 1-pyrrolinyl, 1-pyrrolidinyl, 1-imidazolinyl, 1 imidazolidinyl, 1-pyrazolinyl, 1-pyrazolidinyl, piperidino, morpholino and the following groups are exemplified. Any position that can be substituted in each ring may be substituted.

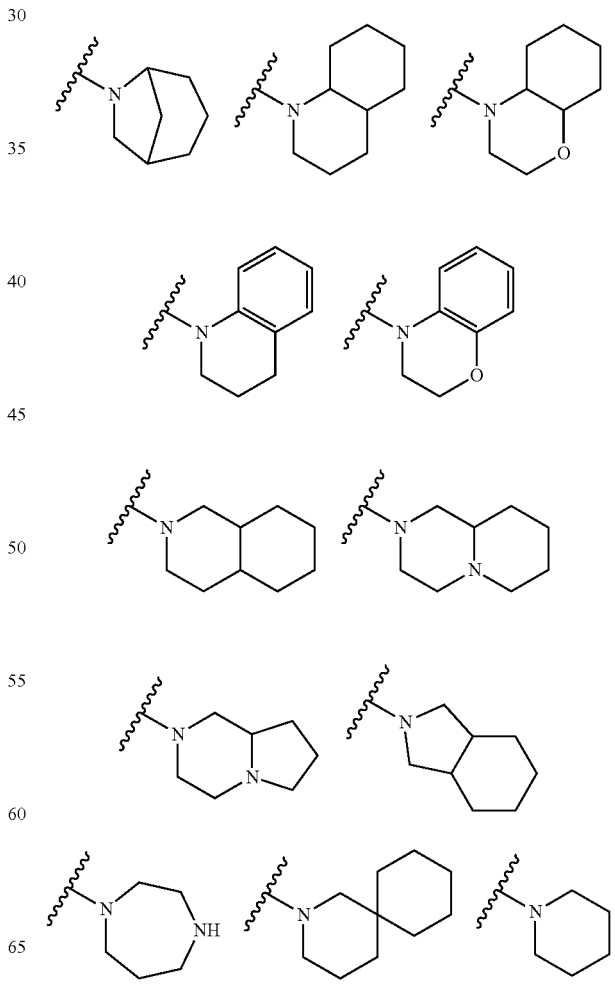

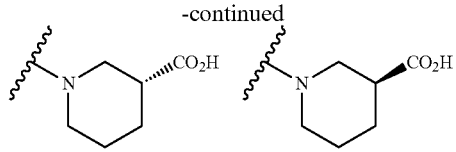
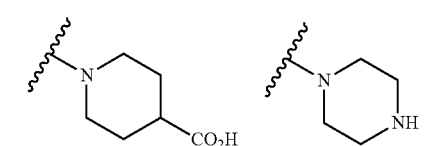
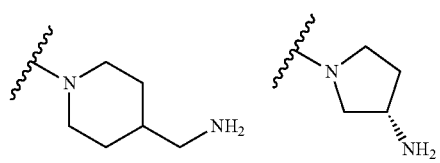
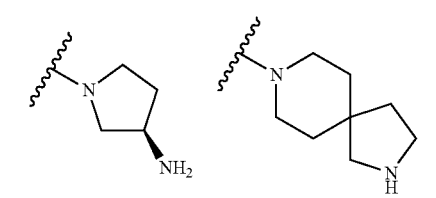
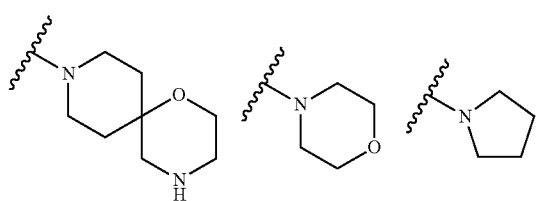

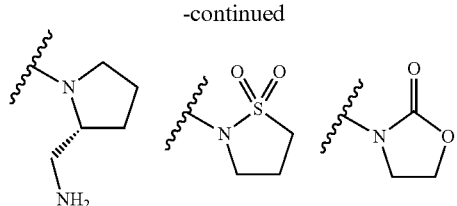
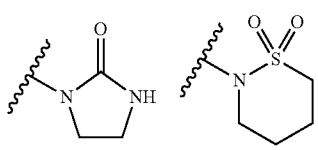

X is hydroxy or a leaving group.

The "leaving group" is not limited as long as it is a substituent which leaves when carboxylic acid and amine are condensed. Example includes halogen, acyloxy (e.g., acetyloxy, benzoyloxy or the like), substituted or unsubstituted alkylsulfonyloxy (e.g., methanesulfonyloxy, trifluoromethanesulfonyloxy or the like), substituted or unsubstituted benzene sulfonyloxy (e.g., paratoluene sulfonyloxy, orthonitrobenzene sulfonyloxy or the like), N,N'-dicyclohexylcarbamimidoyloxy, N,N'-diisopropylcarbamimidoyloxy, (N-(3-(dimethylamino)propyl)-N'-ethylcarbamimidoyloxy or the like.

Preferable is halogen. Especially, preferable is chloro.

Among the compounds of the present invention, the compound represented by the Formula (I) means a mixture of the compound (anti isomer) represented by the Formula (II) and the compound (syn isomer) represented by the Formula (II').

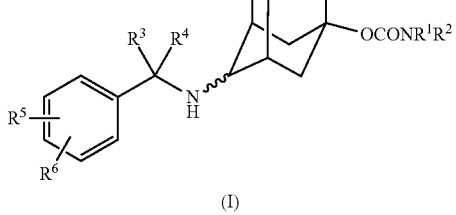

(I)

=

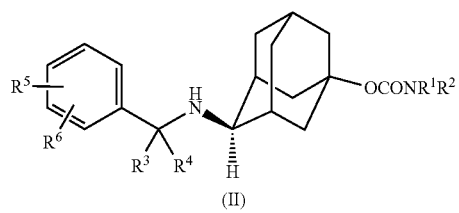

(II)

+

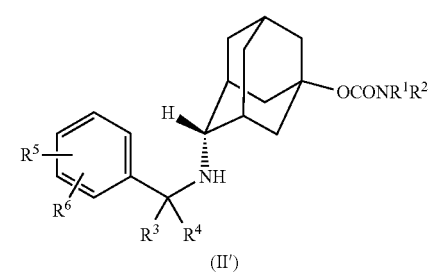

(II')

One or more hydrogen, carbon or other atoms of the compound of formula (I) to (VIII) of the present invention can be replaced by an isotope of the hydrogen, carbon or other atoms.

For example, compounds of formula (I) include all radiolabeled forms of compounds of formula (I). The "radiolabeled", "radiolabeled form" and the like of the compound of formula (I) are encompassed by the present invention and useful as a research and/or diagnostic tool in metabolism pharmacokinetic studies and in binding assays.

Examples of isotopes that can be incorporated into the compound of formula (I) of the present invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{38}Cl$, respectively. Radiolabeled compounds of the present invention can be prepared by methods known in the art. For example, tritiated compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in *Isotopes in the Physical and Biomedical Sciences, Vol.* 1, *Labeled Compounds* (*Part A*), Chapter 6 (1987). $^{14}C$-labeled compounds can be prepared by employing starting materials having a $^{14}C$ carbon.

As a salt of the present compound, the following salts can be included.

As a basic salt, example includes alkali metal salt such as sodium salt or potassium salt; alkaline earth metal salt such as calcium salt or magnesium salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as benzoate, acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like. An acid addition salt of this description includes the above acidic salt.

The compound of the present invention or its salt can form a solvate and/or a crystal polymorph, and the present invention contains such solvates and crystal polymorph of various types. A solvate means a solvate of the compound of the present invention or its salt, and example includes solvate of which solvent is alcohol (e.g., ethanol), hydrate, solvate of which solvent is toluene or the like. Example of hydrate includes mono-hydrate, dihydrate or the like. A solvate may be coordinated with an arbitrary number of solvent molecules (e.g., water molecules) in the compound of the present invention. The compound of the present invention or its salt may be left in the atmosphere to absorb moisture, and a case where adsorbed water is attached or a case where hydrate is formed may arise. Moreover, the compound of the present invention or its salt may be recrystallized to form their crystal polymorph.

The term "inhibition" means that the compound of the present invention inhibits the action of 11βHSD-1.

A general method for producing a compound of the present invention will be illustrated below. For extraction, purification and the like, treatment which is carried out in common experiments in organic chemistry may be carried out.

A compound represented by the Formula (IV) can be synthesized as follows.

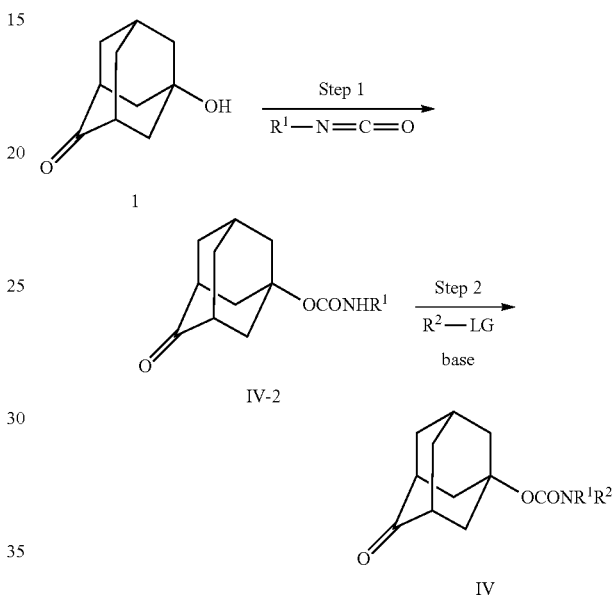

wherein, each symbol has the same meaning as above, and "LG" means a leaving group, and its example includes halogen (fluorine, chlorine, bromine, iodine), tosyl group, mesyl group or the like.

Step 1

Step 1 is a step for producing a compound represented by the Formula (IV-2) by reacting a Compound 1 (5-hydroxy-2-adamantanone) and a compound represented by the formula: $R^1$—N=C=O.

As a Compound 1, a known compound can be used and a compound which is derived from a known compound by a conventional method can be used.

As a solvent, example includes an aprotic polar solvent (e.g., N,N-dimethylformamide, 1-methyl-2-pyrrolidone, N,N-dimethylacetamide), dimethylsulfoxide, aromatic hydrocarbons (e.g., toluene, benzene, xylene or the like), saturated hydrocarbons (e.g., cyclohexane, hexane or the like), halogenated hydrocarbons (e.g., dichloromethane, chloroform, 1,2-dichloroethane or the like), ethers (e.g., tetrahydrofuran, diethyl ether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), alcohols (e.g., methanol, ethanol, t-butanol or the like), water, a mixed solvent thereof or the like.

Preferably, N,N-dimethylformamide, dimethylsulfoxide, aromatic hydrocarbons (e.g., toluene, benzene, xylene or the like), saturated hydrocarbons (e.g., cyclohexane, hexane or the like), halogenated hydrocarbons (e.g., dichloromethane, chloroform, 1,2-dichloroethane or the like), ethers (e.g., tetrahydrofuran, diethyl ether, dioxane, 1,2-dimethoxyethane or the like), esters (e.g., methyl acetate, ethyl acetate or the like), ketones (e.g., acetone, methylethylketone or the like), nitriles (e.g., acetonitrile or the like) or a mixed solvent thereof can be used. In particular, acetone is preferable.

Reaction temperature is in the range of −20 to 50° C., preferably −10 to 20° C., and, in particular, preferably −5 to 5° C.

Reaction time is in the range of 0.5 to 24 hours, preferably 0.5 to 12 hours, and, in particular, preferably 0.5 to 2.5 hours.

Step 2

Step 2 is a step for producing a compound represented by the Formula (IV) by reacting a compound represented by the Formula (IV-2) and a compound represented by the formula: $R^2$-LG.

This reaction is well-known, and any solvent described in Step 1 can be used as a solvent.

Preferably, N,N-dimethylformamide, dimethylsulfoxide, aromatic hydrocarbons (e.g., toluene, benzene, xylene or the like), saturated hydrocarbons (e.g., cyclohexane, hexane or the like), halogenated hydrocarbons (e.g., dichloromethane, chloroform, 1,2-dichloroethane or the like), ethers (e.g., tetrahydrofuran, diethyl ether, dioxane, 1,2-dimethoxyethane or the like), esters (e.g., methyl acetate, ethyl acetate or the like), ketones (e.g., acetone, methylethylketone or the like), nitriles (e.g., acetonitrile or the like) or a mixed solvent thereof can be used.

As a base, example includes metal hydrides (e.g., sodium hydride or the like), metal hydroxides (e.g., sodium hydroxide, potassium hydroxide, lithium hydroxide, barium hydroxide or the like), metal carbonates (e.g., sodium carbonate, calcium carbonate, cesium carbonate or the like), metal alkoxides (e.g., sodium methoxide, sodium ethoxide, potassium t-butoxide or the like), sodium hydrogen carbonate, metal sodium, metal amide, organic amines (e.g., triethylamine, diisopropylethylamine, DBU, pyridine, 2,6-lutidine or the like) and alkyllithiums (n-BuLi, sec-BuLi, tert-BuLi), or the like.

Preferably, metal hydrides (e.g., sodium hydride or the like), metal hydroxides (e.g., sodium hydroxide, potassium hydroxide, lithium hydroxide, barium hydroxide or the like), metal carbonates (e.g., sodium carbonate, calcium carbonate, cesium carbonate or the like), metal alkoxides (e.g., sodium methoxide, sodium ethoxide, potassium t-butoxide or the like) or organic amines (e.g., triethylamine, diisopropylethylamine, DBU, pyridine, 2,6-lutidine or the like) can be used.

Reaction temperature is in the range of −78 to 80° C., preferably −50 to 50° C., and, in particular, preferably −20 to 20° C.

Reaction time is in the range of 0.5 to 24 hours, preferably 0.5 to 12 hours, and, in particular, preferably 0.5 to 3 hours.

Example of $R^2$-LG includes methane chloride or the like.

A compound represented by the Formula (IV-1) can be produced by using a compound (chlorosulfonyl isocyanate) represented by the formula: $ClSO_2$—N=C=O as a compound represented by the formula: $R^1$—N=C=O used in Step 1, followed by conducting hydrolysis.

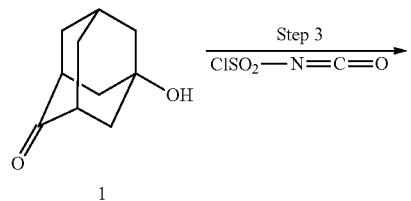

$$\xrightarrow[\text{ClSO}_2-\text{N}=\text{C}=\text{O}]{\text{Step 3}}$$

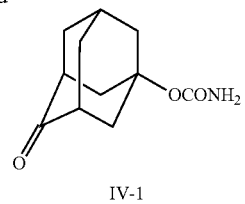

IV-1

Step 3

Step 3 is a step for producing a compound represented by the Formula (IV-1) by reacting a Compound 1 (5-hydroxy-2-adamantanone) and a compound (chlorosulfonyl isocyanate) represented by the formula: $ClSO_2$—N=C=O, followed by conducting hydrolysis.

The hydrolysis can be conducted by adding water to the reaction solution resulting after Step 3.

Time duration for conducting hydrolysis is in the range of 0.5 to 24 hours, preferably 2 to 18 hours, and, in particular, preferably 5 to 12 hours.

Reaction temperature is in the range of −20 to 50° C., preferably −10 to 30° C., and, in particular, preferably 0 to 20° C.

In order to eliminate hydrochloric acid and sulfuric acid produced in the reaction solution as working-up, the reaction solution is neutralized with aqueous ammonia, followed by eliminating the resulting ammonium chloride and ammonium sulfate by liquid separation. Then, water is added to the organic layer, and crystallization by concentration is conducted.

Crystallization time is in the range of 0.5 to 24 hours, preferably 0.5 to 8 hours, and, in particular, preferably 0.5 to 2 hours.

Crystallization temperature is in the range of −20 to 50° C., preferably −10 to 30° C., and, in particular, preferably 15 to 25° C.

A compound represented by the Formula (I) can be synthesized as follows.

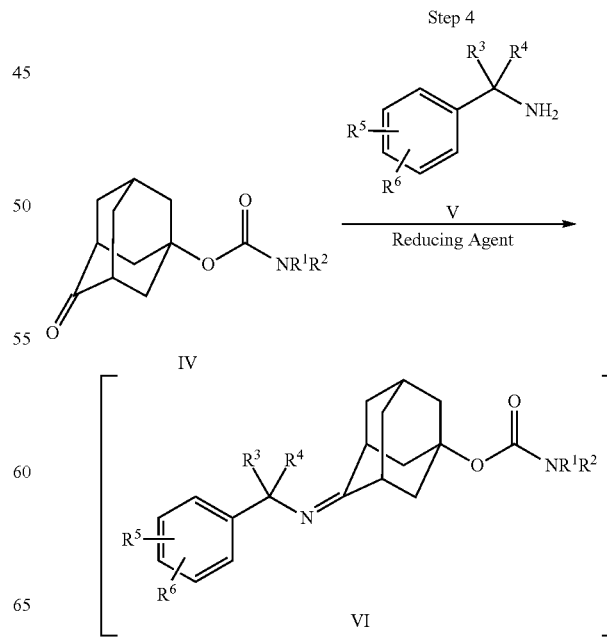

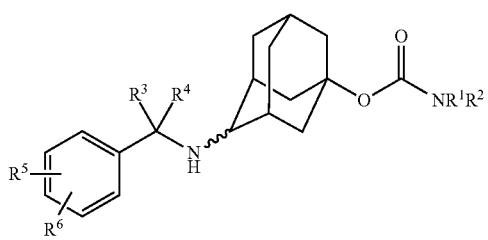

wherein, each symbol has the same meaning as above.

Step 4

Step 4 is a step where a compound represented by the Formula (IV) is reacted with a compound represented by the Formula (V) in the presence of a reducing agent.

Any solvent described in Step 1 can be used as a solvent. Preferably, N,N-dimethylformamide, dimethylsulfoxide, halogenated hydrocarbons (e.g., dichloromethane, chloroform, 1,2-dichloroethane or the like), nitriles (e.g., acetonitrile or the like), ethers (e.g., tetrahydrofuran, diethyl ether, dioxane, 1,2-dimethoxyethane or the like), alcohols (e.g., methanol, ethanol, isopropanol, tert-butanol or the like), water or the like can be used.

More preferably, dichloromethane, chloroform, 1,2-dichloroethane, diethyl ether, dioxane, 1,2-dimethoxyethane, acetonitrile, methanol, ethanol, isopropanol, tert-butanol, tetrahydrofuran or water can be used.

Particularly preferable is dichloromethane, acetonitrile, methanol or ethanol.

Reaction in the step proceeds without an acid, but preferably it is used. Acid such as acetic acid, formic acid, citric acid, paratoluenesulfonic acid, methanesulfonic acid, trifluoroacetic acid, phosphoric acid, hydrochloric acid or sulfuric acid can be used. Preferably, acetic acid is used.

The reaction solution is not particularly limited, but in order to form an imine body represented by the Formula (VI), the solution can be stirred usually at about 0 to 80° C., preferably at about 40 to 60° C., usually for 5 minutes to 5 hours, preferably for 90 minutes to 2 hours.

The reaction solution thus prepared, although not particularly limited, is cooled to about −20 to 20° C., preferably to about 0 to 10° C., and then is reduced.

The reduction can be carried out by using, for example, hydride reducing agent. The hydride reducing agent means a reagent capable of providing hydrogen as a nucleophilic agent. As a hydride reducing agent, sodium tri(acetoxy)hydroborate, sodium borohydride, lithium tetrahydroborate, pyridine borane complex, tetrahydrofuran borane complex, 2-picoline borane complex, dimethyl sulfide borane complex, sodium cyanoborohydride, lithium triethylborohydride, lithium aluminium hydride, Red-Al [sodium bis(2-methoxyethoxy)aluminum hydride], L-Selectride [lithium tri(sec-butyl)borohydride], K-Selectride [potassium tri(sec-butyl)borohydride], DIBAL-H (diisobutylaluminium hydride), tributyltin hydride or the like can be used.

Preferably, sodium tri(acetoxy)hydroborate, sodium borohydride, lithium tetrahydroborate, pyridine borane complex, tetrahydrofuran borane complex, 2-picoline borane complex, sodium cyanoborohydride, lithium aluminium hydride, or Red-Al can be used.

More preferably, sodium tri(acetoxy)hydroborate, sodium borohydride, or sodium cyanoborohydride can be used. The amount used is not particularly limited, but 0.3 to 15 equivalents, preferably 0.5 to 10 equivalents can be used.

Time duration for conducting reduction is in the range of 0.5 to 24 hours, preferably 0.5 to 12 hours, and, in particular, preferably 0.5 to 2 hours.

The reaction temperature is not particularly limited, but the solution is cooled to about −20 to 20° C., preferably to about 0 to 10° C., and then is reduced.

An acid is added to a reaction solution containing a compound represented by the Formula (I) to make the solution acidic, followed by neutralizing.

In reductive amination, besides the reduction using the hydride reducing agent, reduction can be conducted by hydrogenation reaction in the presence of a catalyst. As a catalyst, ruthenium, rhodium, palladium, platinum or nickel can be used.

Moreover, reductive amination using sodium can also be conducted.

An acid addition salt of a compound represented by the Formula (II), or a solvate of the acid addition salt can be synthesized as follows.

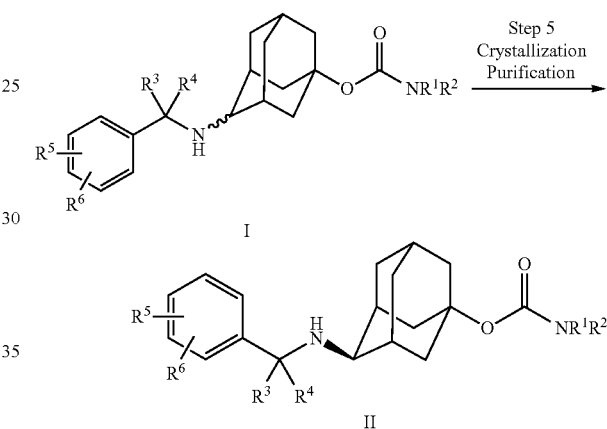

wherein, each symbol has the same meaning as above.

Step 5

Step 5 is a step where anti isomer represented by the Formula (II) is separated from a mixture of anti isomer and syn isomer represented by the Formula (I). The step can be conducted by crystallization.

The step involves adding an acid in order to form an acid addition salt of a compound represented by the Formula (II) or a solvate of the acid addition salt. As an acid, hydrochloric acid, benzoic acid, sulfuric acid, nitric acid, acetic acid, citric acid, oxalic acid, phosphoric acid, carbonic acid, perchloric acid, acetic acid, propionic acid, lactic acid, maleic acid, fumaric acid, tartaric acid, malic acid, ascorbic acid, methanesulfonic acid, isethionic acid, benzenesulfonic acid, p-toluenesulfonic acid, aspartic acid, glutamic acid or the like can be used. Preferably, hydrochloric acid or benzoic acid can be used. The amount of the acid used is not particularly limited, but, for example, 0.1 to 2 equivalents, preferably 0.5 to 1 equivalents, more preferably 0.5 to 0.9 equivalents can be added to a compound represented by the Formula (I).

Crystallization of an acid addition salt of a compound represented by the Formula (II) or a solvate of the acid addition salt can be conducted by forming the acid addition salt in any soluble solvent of a compound represented by the Formula (I), followed by precipitating crystals by adding poor solvent if necessary.

As the soluble solvent, for example, N,N-dimethylformamide, dimethylsulfoxide, aromatic hydrocarbons (e.g., toluene, benzene, xylene or the like), saturated carbon hydrides (e.g., cyclohexane, hexane or the like), halogenated hydrocarbons (e.g., dichloromethane, chloroform, 1,2-dichloroethane or the like), ethers (e.g., tetrahydrofuran, diethyl ether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), a mixed solvent thereof or the like can be used.

Preferably, N,N-dimethylformamide, aromatic hydrocarbons (e.g., toluene, benzene, xylene or the like), halogenated hydrocarbons (e.g., dichloromethane, chloroform, 1,2-dichloroethane or the like), esters (e.g., methyl acetate, ethyl acetate or the like), ketones (e.g., acetone, methylethylketone or the like), nitriles (e.g., acetonitrile or the like) or a mixed solvent thereof can be used.

Preferably, the solvent where a compound represented by the Formula (I) dissolves with high solubility, and an acid addition salt of a compound represented by the Formula (II) or a solvate of the acid addition salt dissolves with low solubility is preferred.

The step of separating an acid addition salt of a compound represented by the Formula (II) or a solvate of the acid addition salt from a mixture of syn isomer and anti isomer of a compound represented by the Formula (I) in the solvent comprises the following steps. For example, a step of precipitating an acid addition salt of a compound represented by the Formula (II) or a solvate of the acid addition salt by adding an acid, in the presence of a solvent, to a mixture of syn isomer and anti isomer of a compound represented by the Formula (I); a step of precipitating an acid addition salt of a compound represented by the Formula (II) or a solvate of the acid addition salt by adding a solvent containing an acid to a mixture of syn isomer and anti isomer of a compound represented by the Formula (I); and a step of precipitating an acid addition salt of a compound represented by the Formula (II) or a solvate of the acid addition salt by adding a solvent containing an acid and further adding a poor solvent to a mixture of syn isomer and anti isomer of a compound represented by the Formula (I); or the like can be included.

In the case where crystallization can be conducted with a soluble solvent alone, a poor solvent does not need to be used. However when a poor solvent is used, as the poor solvent, for example, aromatic hydrocarbons (e.g., toluene, benzene, xylene or the like), saturated hydrocarbons (e.g., cyclohexane, hexane or the like), ethers (e.g., tetrahydrofuran, diethyl ether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), a mixed solvent thereof or the like can be used. Preferably, aromatic hydrocarbons (e.g., toluene, benzene, xylene or the like), halogenated hydrocarbons (e.g., dichloromethane, chloroform, 1,2-dichloroethane or the like) or esters (e.g., methyl acetate, ethyl acetate or the like) can be used. More preferably, toluene, dichloromethane or ethyl acetate can be used.

The crystallization, although not particularly limited, can be stirred at −78 to 80° C., preferably at 0 to 60° C.

The resulting crystals can be obtained by filtration or the like. At this point, the syn isomer is dissolved in the filtrate, thus purification effect by the crystallization is produced.

For example, when hydrochloric acid is used as an acid, crystals of hydrochloride of a compound represented by the Formula (II) or a solvate of the hydrochloride can be obtained. Particularly, crystals of hydrochloride of a compound represented by the Formula (II) can be obtained.

For example, when benzoic acid is used as an acid and toluene as a solvent, crystals of benzoate of a compound represented by the Formula (II) or toluene-solvated benzoate can be obtained. Particularly, crystals of toluene-solvated benzoate of a compound represented by the Formula (II), and moreover, crystals of toluene-hemisolvated benzoate of a compound represented by the Formula (II) can be obtained.

These crystals of hydrochloride of a compound represented by the Formula (II) and crystals of toluene-hemisolvated benzoate of a compound represented by the Formula (II) are extremely highly crystallized, thus are very important intermediates to obtain a compound represented by the Formula (II) or a compound represented by the Formula (III) with high purity.

By using these acid addition salts, the ratio of anti isomer in a mixture of anti isomer and syn isomer can be made to be 95% or higher. The ratio is preferably 97% or higher, more preferably 98% or higher.

The present invention includes compounds represented by the Formula (I) where the ratio of anti isomer to syn isomer falls in the range of 95-100 to 0-5, compounds represented by the Formula (II) where syn isomer constitutes 5% or less, compounds represented by the Formula (III) where syn isomer constitutes 5% or less, and compositions containing these compounds.

Moreover, the present invention includes compounds represented by the Formula (I) where the ratio of anti isomer to syn isomer falls in the range of 97-99 to 3-1, compounds represented by the Formula (II) where syn isomer constitutes 1-3%, compounds represented by the Formula (III) where syn isomer constitutes 1-3%, and compositions containing these compounds.

A compound represented by the Formula (III), its salt, or a solvate thereof can be synthesized as follows.

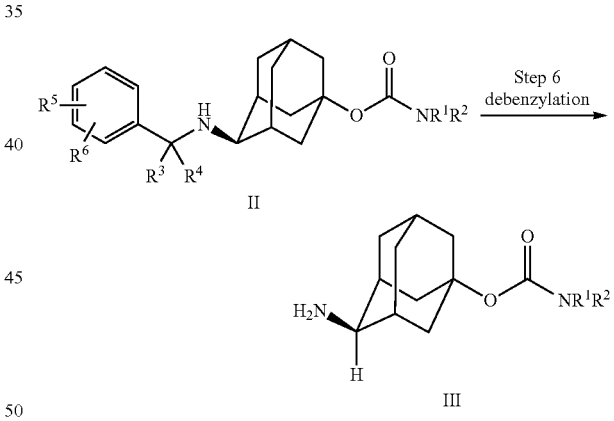

wherein, each symbol has the same meaning as above.

Step 6

Step 6 is a step for producing a compound represented by the Formula (III), its salt, or a solvate thereof by debenzylating an acid addition salt of a compound represented by the Formula (II) or a solvate of the acid addition salt.

Any solvent described in Step 1 can be used as a solvent. Preferably, ethers (e.g., tetrahydrofuran, diethyl ether, dioxane, 1,2-dimethoxyethane or the like) or alcohols (e.g., methanol, ethanol, isopropanol, tert-butanol or the like) can be used. Particularly, methanol is preferable. The amount of solvent used is not particularly limited, and any amount capable of forming a solution that can carry out a reaction is usable. A heterogeneous catalyst can be added to a solution thus prepared, and a catalytic reduction can be conducted in the presence of hydrogen gas.

As the heterogeneous catalyst, for example, palladium/carbon catalyst, platinum/carbon catalyst, rhodium, ruthenium, palladium, platinum, nickel or the like can be used. The amount used is not particularly limited, but 0.001 to 1 equivalents, preferably 0.01 to 1 equivalents can be used.

The step can be carried out in the presence of an acid. The acid is preferably hydrochloric acid. For example, when toluene-hemisolvated benzoate of a compound represented by the Formula (II) is debenzylated, precipitation of benzoate of a compound represented by the Formula (III) can be prevented by conducting the reaction in the presence of an acid. The amount of added acid can be 0.5 to 2 equivalents for the acid addition salt of a compound represented by the Formula (II) or the solvate of the acid addition salt. For example, when about 1 equivalent of acid is used, catalytic reduction can be conducted in the presence of about 0.4 to 0.6 equivalents of an acid, and after eliminating the catalyst, about 0.4 to 0.6 equivalents of an acid can be added.

Reaction temperature is in the range of 0 to 80° C., preferably 10 to 60° C., and, in particular, preferably 20 to 50° C.

Reaction time is in the range of 0.5 to 24 hours, preferably 1 to 18 hours, and, in particular, preferably 2 to 6 hours.

The step can be conducted under hydrogen gas atmosphere at ordinary pressure, but it can alternatively be conducted under pressurized atmosphere.

A compound represented by the Formula (VII-2) can be synthesized as follows.

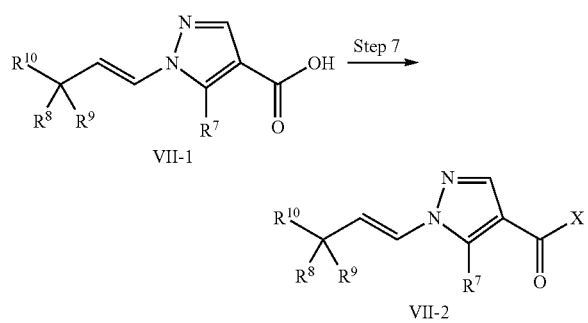

wherein X is a leaving group, other symbol has the same meaning as above, and a compound represented by the Formula (VII-1), a known compound can be used and a compound which is derived from a known compound by a conventional method can be used. Details of the compound represented by the Formula (VII-1) and process for producing the same are described in WO2007/058346 and WO2008/142986.

Step 7

Step 7 is a step for producing a compound represented by the Formula (VII-2) from a compound represented by the Formula (VII-1)

When X is halogen, a halogenating agent can be reacted with the compound represented by the Formula (VII-1).

As a halogenating agent, phosphorous oxychloride, phosphorous pentachloride, oxalyl chloride, thionyl chloride, sulfuryl chloride, dichlorotriphenylphosphorane or the like can be used. The agent is, in particular, preferably phosphorous oxychloride, phosphorous pentachloride, oxalyl chloride or thionyl chloride.

Any solvent described in Step 1 can be used as a solvent. Preferably, 1-methyl-2-pyrrolidone, dichloromethane, toluene, benzene, tetrahydrofuran, chloroform, dimethylformamide, acetonitrile, diethyl ether, benzene, xylene, cyclohexane, hexane, ethyl acetate, butyl acetate, pentane, heptane, dioxane, acetone, water, a mixed solvent thereof or the like can be used. The solvent is, in particular, preferably 1-methyl-2-pyrrolidone, toluene, tetrahydrofuran or dimethylformamide.

The reaction can be conducted at about −20 to 100° C., preferably at −5 to 10° C. Reaction time is in the range of 0.5 to 20 hours, preferably 0.5 to 10 hours.

In Step 7 stated above, by using a reagent other than a halogenating agent, a compound represented by the Formula (VII-2) each having a different leaving group can be synthesized. For example, by reacting acyl halide with a compound represented by the Formula (VII-1) in the presence of a base, a compound represented by the Formula (VII-2) having acyloxy as a "leaving group" can be produced. By reacting substituted or unsubstituted alkylsulfonyl halide with a compound represented by the Formula (VII-1) in the presence of a base, a compound represented by the Formula (VII-2) having substituted or unsubstituted alkylsulfonyloxy as a "leaving group" can be produced. The same holds true for others.

A compound represented by the Formula (VIII) can be synthesized as follows.

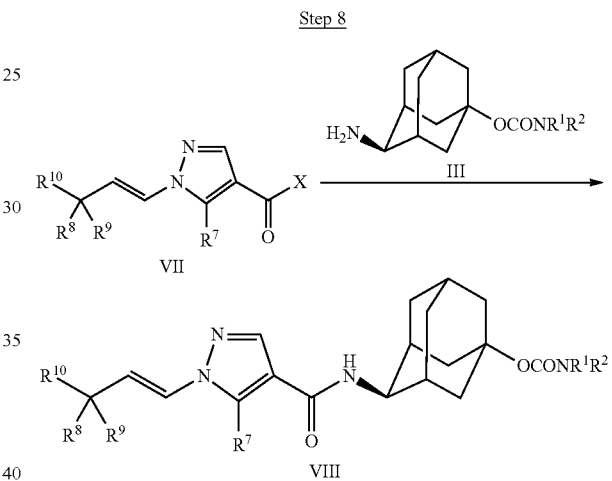

wherein, each symbol has the same meaning as above, and as a compound represented by the formula (VII), a known compound can be used and a compound which is derived from a known compound by a conventional method can be used.

Step 8

Step 8 is a step for producing a compound represented by the Formula (VIII) by reacting a compound represented by the Formula (VII) and a compound represented by the Formula: (III).

When X is hydroxy, the step can be carried out in the presence of a condensing agent.

As a condensing agent, an amide condensing agent used in condensation of carboxyl group and amino group can be used. For example, carbodiimides (for example, N,N'-dicyclohexylcarbodiimide, N,N'-diisopropylcarbodiimide, 1-ethyl-3-(3-dimethylaminopropyl)carbodiimide hydrochloride or the like), diphenylphosphoryl azide, BOP reagents (for example, BOP, PyBop, TBTU or the like), DMT-MM, 1,1'-carbonyl-bis-1H-imidazole, 2-chloro-1,3-dimethylimidazolium chloride, 4-(4,6-dimethoxy-1,3,5-triazin-2-yl)-4-methylmorpholinium chloride or the like can be used. Preferably, the agent is N,N'-dicyclohexylcarbodiimide, N,N'-diisopropylcarbodiimide, or 1-ethyl-3-(3-dimethylaminopropyl)carbodiimide hydrochloride, and in particular, preferably 1-ethyl-3-(3-dimethylaminopropyl)carbodiimide hydrochloride.

The step can be carried out in the presence of an additive.

As an additive, 1-hydroxybenzotriazole, N-hydroxysuccinimide or the like can be used. The additive is, in particular, preferably 1-hydroxybenzotriazole.

The step can be carried out in the presence of a base. The base can be appropriately selected depending on the type of a leaving group and the type of a reaction solvent.

Example of the base used in the step includes metal hydrides (e.g., sodium hydride or the like), metal hydroxides (e.g., sodium hydroxide, potassium hydroxide, lithium hydroxide, barium hydroxide or the like), metal carbonates (e.g., sodium carbonate, calcium carbonate, cesium carbonate or the like), metal alkoxides (e.g., sodium methoxide, sodium ethoxide, potassium tert-butoxide or the like), sodium hydrogen carbonate, metal sodium, organic amines (e.g., triethylamine, diisopropylethylamine, DBU, 2,6-lutidine or the like), pyridine, imidazole, diazabicycloundecene or the like. The base is preferably triethylamine, diisopropylethylamine, diazabicycloundecene or the like, and, in particular, preferably triethylamine.

The step can be carried out at −20 to 200° C. Preferably, the step can be carried out at 0 to 100° C.

As a solvent, example includes water, alcohols (e.g., methanol, ethanol, t-butanol or the like), halogenated hydrocarbons (e.g., dichloromethane, chloroform, 1,2-dichloroethane or the like), aromatic hydrocarbons (e.g., toluene, benzene, xylene or the like), aprotic polar solvents (e.g., N,N-dimethylformamide, 1-methyl-2-pyrrolidone, N,N-dimethylacetamide), ethers (e.g., tetrahydrofuran, diethyl ether, dioxane, 1,2-dimethoxyethane or the like), nitriles (e.g., acetonitrile or the like) or the like. The solvent is, in particular, preferably dichloromethane or N,N-dimethylformamide.

When X is a leaving group derived from halogen or hydroxyl group, any base stated above can be used in the step. The base is preferably metal hydroxides (e.g., sodium hydroxide, potassium hydroxide, lithium hydroxide, barium hydroxide or the like), metal carbonates (e.g., sodium carbonate, calcium carbonate, cesium carbonate or the like) or sodium hydrogen carbonate or the like. The base is, in particular, preferably sodium hydroxide, sodium carbonate or sodium hydrogen carbonate or the like.

Any solvent described in Step 1 can be used as a solvent. Preferably, N,N-dimethylformamide, 1-methyl-2-pyrrolidone, dimethylsulfoxide, aromatic hydrocarbons (e.g., toluene, benzene, xylene or the like), halogenated hydrocarbons (e.g., dichloromethane, chloroform, 1,2-dichloroethane or the like), ethers (e.g., tetrahydrofuran, diethyl ether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), water, a mixed solvent thereof or the like can be used. The solvent is, in particular, preferably N,N-dimethylformamide, 1-methyl-2-pyrrolidone, tetrahydrofuran, ethyl acetate, water, a mixed solvent thereof or the like. Reaction conditions are not particularly limited, but the solvent can be stirred normally for 1 to 36 hours, preferably for 1 to 4 hours, at about −20 to 50° C., preferably at about −10 to 20° C.

The compound represented by the Formula (VII) and the compound represented by the Formula (III) can be used in a form of a salt or a solvate.

Unless otherwise stated, figures indicated in the description and in the claims are approximate. Variations of the figures are attributed to device calibrations, device errors, purity of substances, crystal sizes, sample sizes and other factors.

Various types of substituent of the compounds of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS or the like.

The present invention is further explained by the following Examples, which are not intended to limit the scope of the present invention.

The meaning of each term in Examples is as follows.
CSI: chlorosulfonyl isocyanate
BnNH$_2$: benzylamine
AcOH: acetic acid
DMA: N,N-dimethylacetamide
WSCD HCl: 1-(3-dimethylaminopropyl)-3-ethylcarbodiimide hydrochloride
HOBt: 1-hydroxybenzotriazole.
DMF: N,N-dimethylformamide NMR analysis obtained in each example was measured by 300 MHz, and measured using d6-DMSO or d6-CDCl$_3$.

Powder X-ray diffraction measurements of crystals were conducted under the following measuring conditions in accordance with the powder X-ray diffraction measuring method described in General Tests of the Japanese Pharmacopoeia.
(Device)
TTR III manufactured by Rigaku
(Operation Procedures)
Samples were measured under the following conditions.
Measuring Method: Reflection Method
Type of Light Source: Cu Tube
Wavelength Used CuKα X-ray
Tube Electric Current: 300 mA
Tube Electric Voltage: 50 Kv
Sample Plate: Aluminum
Scan Speed: 5.000°/min.
Scan Range: 4.000 to 40.0000°
Sampling Width: 0.0200°

Generally, a diffraction angle (2θ) in powder X-ray diffraction is susceptible to error in a range of ±0.2°, thus the value of a diffraction angle includes a margin of error of about ±0.2°. Accordingly, the present invention includes not only crystals whose diffraction angles at the peak of powder X-ray diffraction are perfectly same, but also crystals whose diffraction angles at the peak are almost same with a margin of error of ±0.2°.

A compound represented by the Formula (II), a compound represented by the Formula (III), a compound represented by the Formula (IV) and a compound represented by the Formula (VI) are useful as an intermediate to produce a compound represented by the Formula (VIII).

Among these intermediates, crystals described in the present description are, in particular, preferable. For example, crystals with two or more 2θ values selected from values of 2θ (±0.2°) of powder X-ray diffraction presented in the present description, crystals with three or more of those 2θ values, crystals with four or more of those 2θ values, crystals with five or more of those 2θ values, and others are preferable.

Example 1

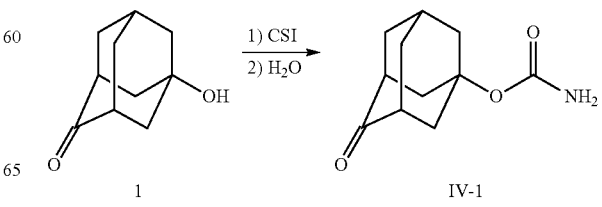

A solution of Compound 1 (5-hydroxy-2-adamantanone) (60.00 g, 360.97 mmol) in acetone (420 ml) was cooled to 0° C., and chlorosulfonyl isocyanate (CSI) (53.6 g, 378.72 mmol) was added thereto for 1 hour. The reaction mixture was stirred for 30 minutes. Then, the solution was kept at 5° C. To the solution was added water (60 ml) for 2 hours, and then the solution was heated to 15° C. The solution was stirred for another 7 hours. To the solution was added 7% ammonia water to obtain pH 7.9. The solution was heated to 60° C., and then was separated. To the extraction solution in the upper layer was added water (240 ml), and the solution was concentrated. Crystallization was conducted for 1 hour at 25° C., and the precipitated crystal was filtered. The obtained crystal was dried to obtain compound (IV-1, 64.43 g, 85.3%).

$^1$H NMR (d6-DMSO); δ (ppm) 1.82 (brd, J=13 Hz, 2H), 1.96 (brd, J=13 Hz, 2H), 2.24 (m, 1H), 2.24 (brs, 2H), 2.27-2.28 (m, 4H), 2.48 (brs, 2H), 6.30 (br, 21-1)

Melting Point: 193 to 194° C.

Powder X-ray Diffraction 2θ (°): 12.2, 16.8, 17.6, 19.0, 21.7, 24.5, 34.2

Figure 2:
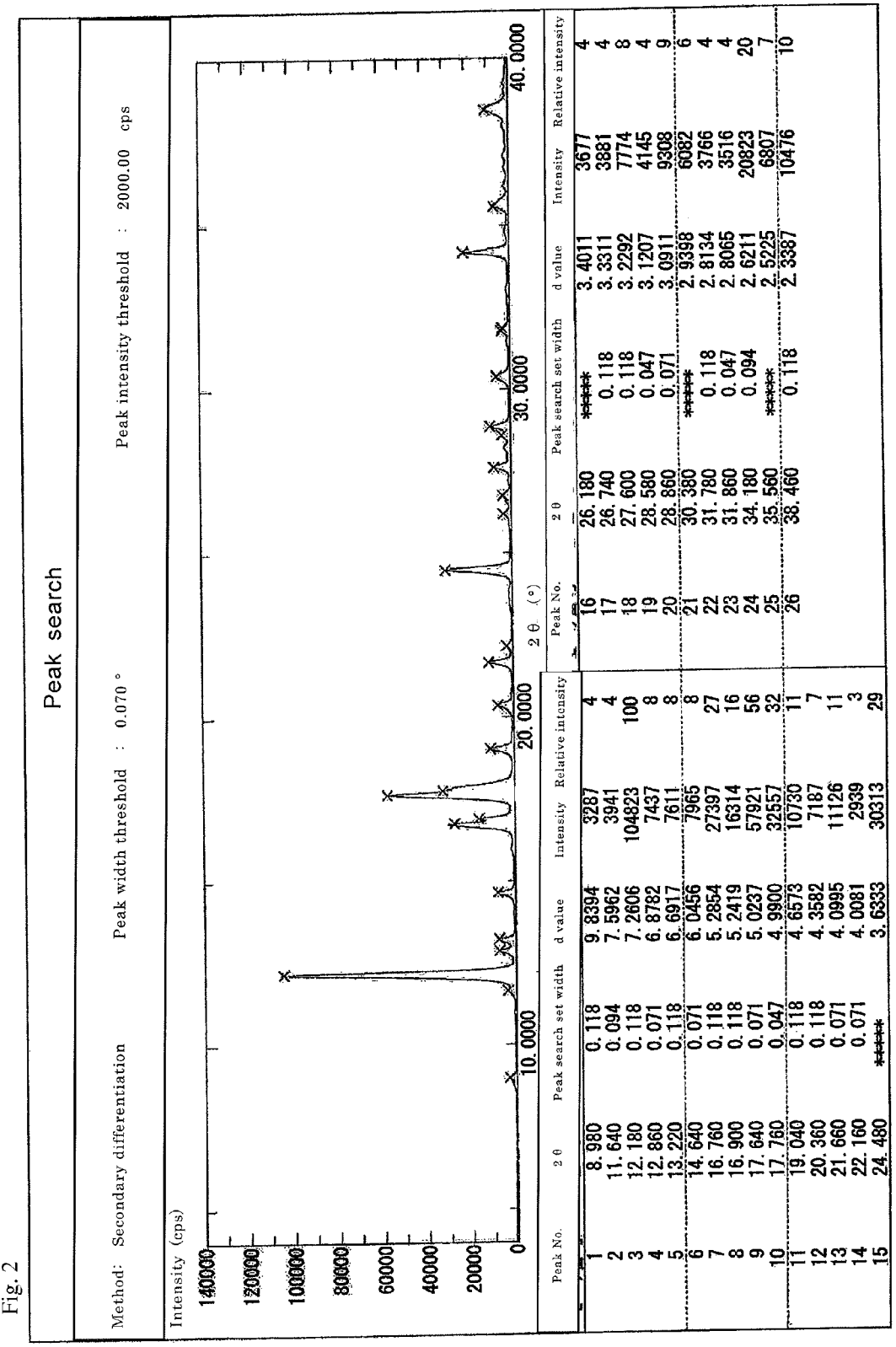
FIG. 2 shows data of powder X-ray diffraction for compound (IV-1).

Results of the powder X-ray diffraction are shown in FIG. 1 and FIG. 2.

Example 2

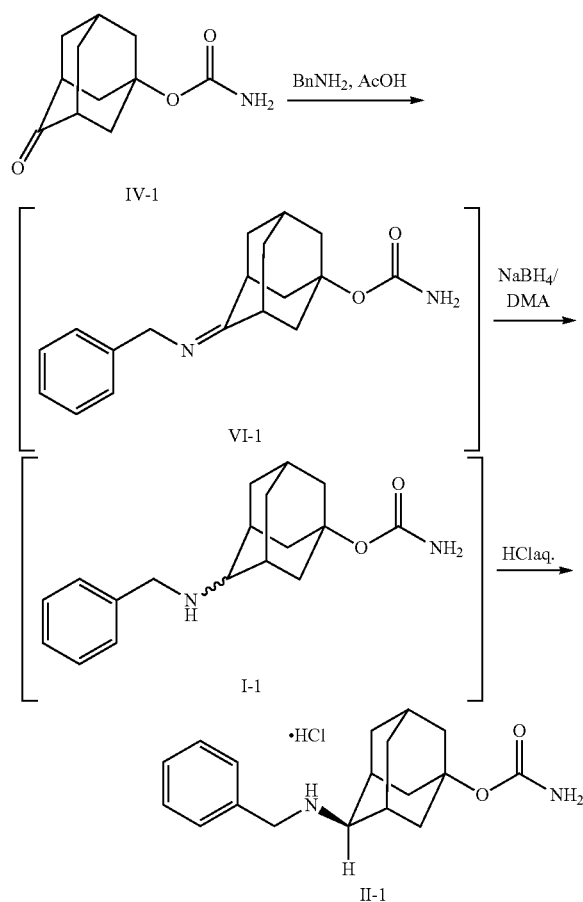

To a solution of Compound IV-1 (30.00 g, 143.4 mmol) in dichloromethane (300 ml) were added benzylamine (15.36 g, 143.4 mmol) and acetic acid (8.61 g, 143.4 mmol), and the reaction mixture was cooled to 0° C.

To the reaction solution containing the resulting Compound VI-1 was added a solution of sodium borohydride (3.25 g, 83.7 mmol) in N,N-dimethylacetamide (45 ml) over 2 hours, and the reaction mixture was stirred for another 2 hours.

To the reaction solution containing the resulting Compound I-1 was added hydrochloric acid (7%) to obtain pH 2, and the reaction mixture was heated to room temperature. To the reaction mixture were added water (150 ml) and 16% sodium hydroxide aqueous solution to obtain pH 8, and the reaction mixture was extracted. The extraction solution in the lower layer was cooled to 5° C., 4N-hydrochloric acid/ethyl acetate solution (35.85 ml, 143.4 mmol) was added thereto. Crystallization was conducted for 2 hours at 5° C. The precipitated crystal was filtered, and dried to obtain compound (II-1, 27.48 g, 56.90%) as hydrochloride.

Compound VI-1: $^1$H NMR (d6-CDCl3); δ (ppm): 1.67 (brd, J=13 Hz, 1H), 1.89 (m, 3H), 2.08 (brd, J=12 Hz, 1H), 2.30 (m, 6H), 2.79 (m, 1H), 3.34 (m, 1H), 4.51 (br, 2H), 4.55 (d, J=3 Hz, 2H), 7.24 (m, 2H), 7.30 (m, 3H)

Compound II-1 (hydrochloride): $^1$H NMR (d6-DMSO); δ (ppm) 1.44 (brd, J=13 Hz, 2H), 2.00 (m, 2H), 2.01 (brs, 2H), 2.07 (brd, J=13 Hz, 2H), 2.09 (m, 1H), 2.15 (brd, J=13 Hz, 2H), 2.40 (brs, 1H), 2.49 (brs, 1H), 3.15 (brs, 1H), 4.17 (brs, 2H), 6.23 (br, 2H), 7.42 (m, 3H), 7.67 (m, 2H), 9.42 (brs, 2H)

Powder X-ray diffraction 2θ (°) of Compound II-1 (hydrochloride): 9.4, 15.6, 16.5, 18.9, 19.8, 21.1, 24.2, 26.5, 28.6

Figure 3:
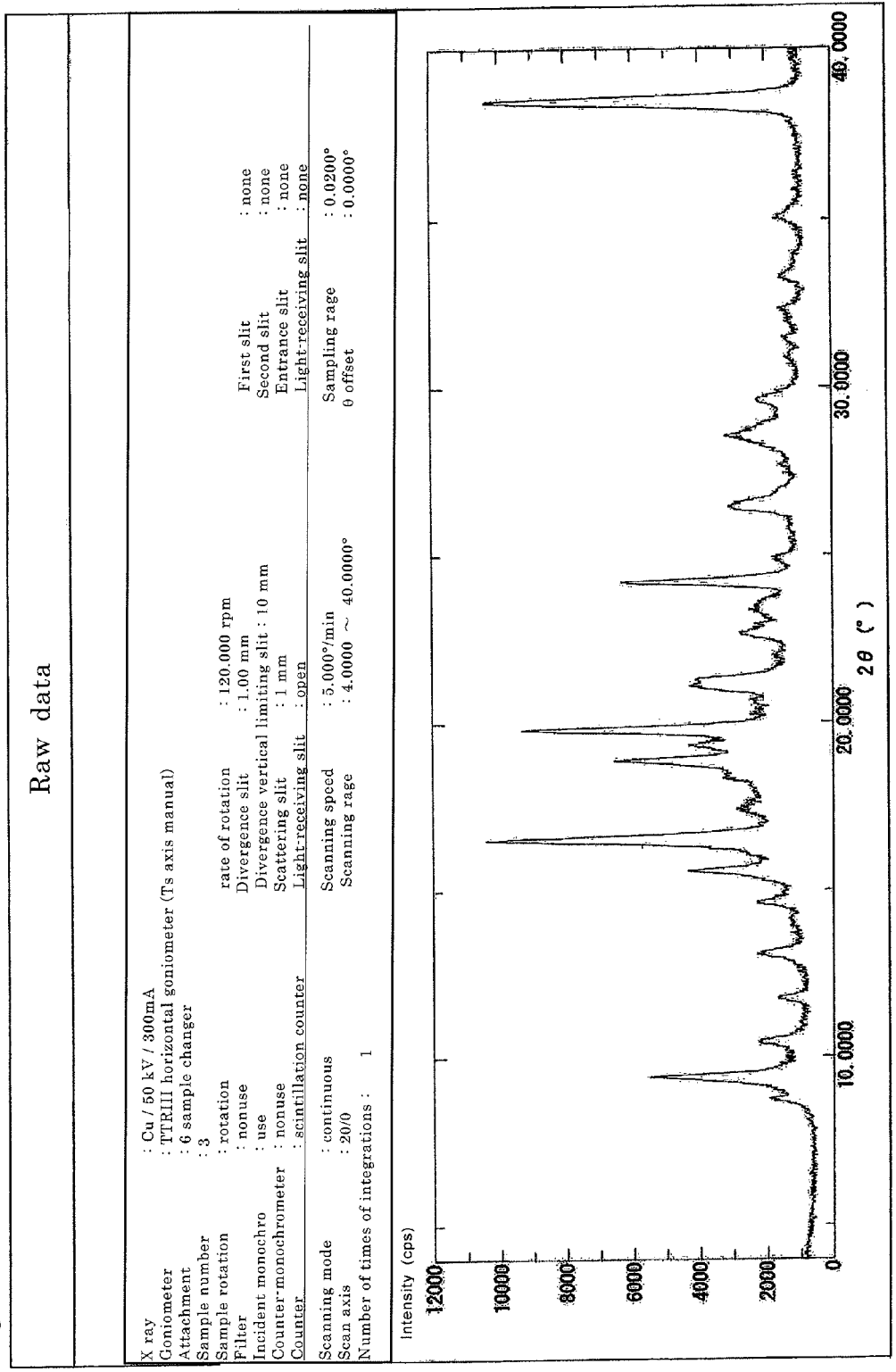
FIG. 3 shows data of powder X-ray diffraction for compound (II-1).
Figure 4:
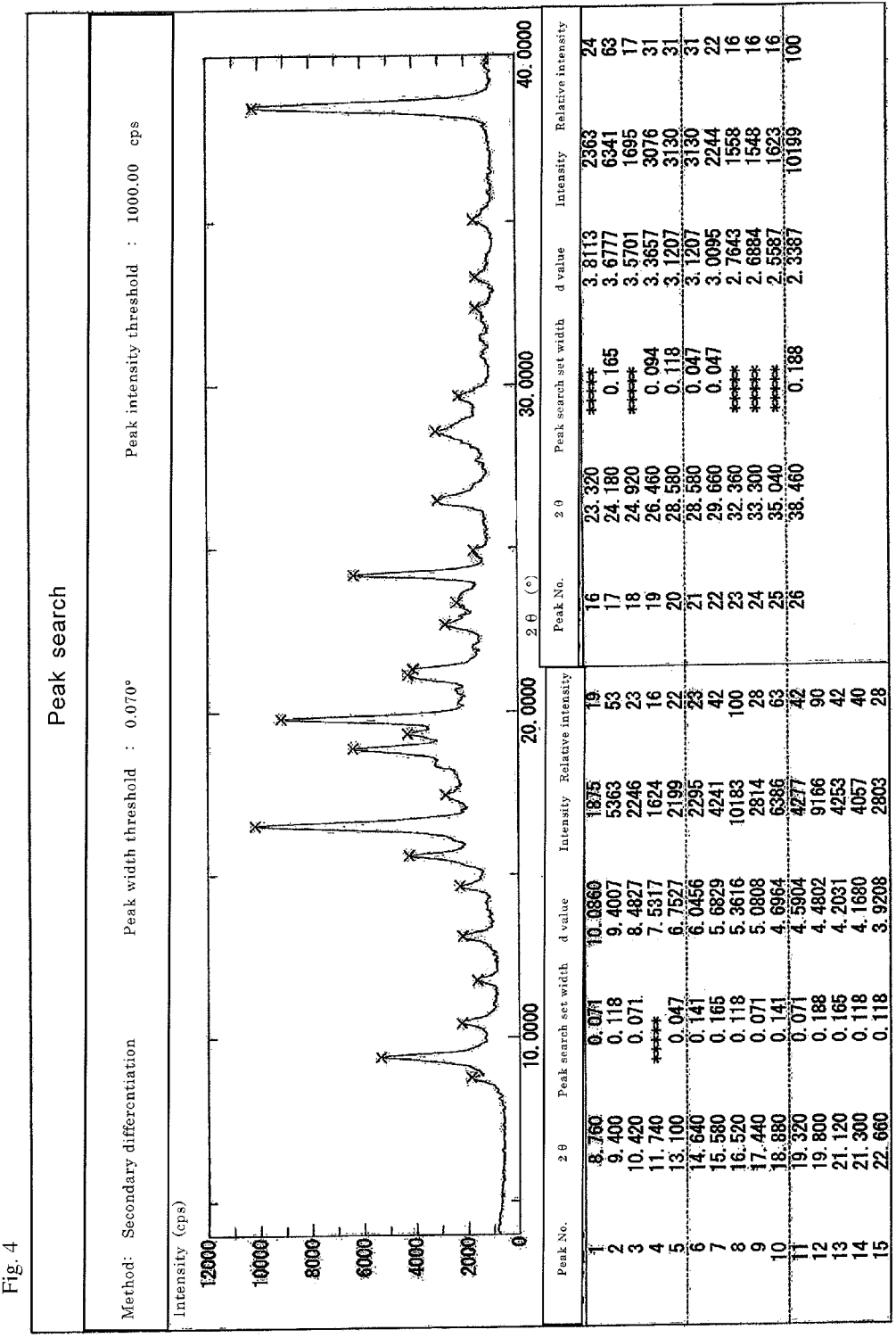
FIG. 4 shows data of powder X-ray diffraction for compound (II-1).

Results of powder X-ray diffraction of Compound II-1 (hydrochloride) are shown in FIG. 3 and FIG. 4.

Compound (I-1) was a mixture where anti isomer and syn isomer existed in a ratio of 4 to 1 (calculated by NMR Analysis (300 MHz)).

On the other hand, Compound (II-1) exhibited significant purification effects by crystallization, and the ratio of anti isomer to syn isomer was 97 to 3.

Example 3

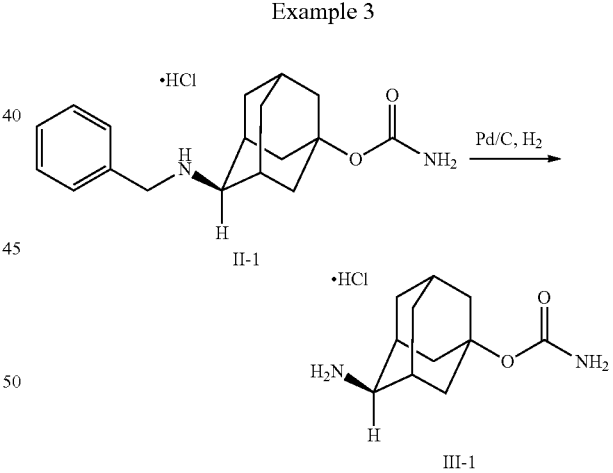

A solution of compound (II-1, 20.00 g, 59.4 mmol) in methanol (200 ml) and 5% palladium carbon catalyst (M) (moisture 53.1%, 4.26 g) were heated to 30° C., and the reaction mixture was stirred for 5 hours under pressure of hydrogen of 0.2 MPa. The reaction solution was filtered to eliminate the palladium carbon catalyst, and then the filtrate was concentrated under reduced pressure. The concentrated solution was replaced with tetrahydrofuran, and was crystallized for 1 hour at room temperature. The precipitated crystal was filtered, and dried to obtain compound (III-1, 12.78 g, 87.3%).

Melting Point: 222.5 to 223.0° C.

$^1$H NMR (d6-DMSO); δ (ppm) 1.45 (brd, J=13 Hz, 2H), 1.98 (brd, J=13 Hz, 2H), 2.04 (m, 1H), 2.05 (br, 1H), 2.07

(brd, J=11 Hz, 2H), 2.12 (brd, J=11 Hz, 2H), 2.20 (br, 2H), 3.29 (m, 1H), 6.23 (br, 2H), 8.32 (brs, 3H)

Powder X-ray Diffraction 2θ (°): 11.9, 14.9, 17.6, 18.4, 18.9, 19.8, 20.4, 23.2, 27.3, 30.1

Element Analysis $C_{11}H_{18}N_2O_2$—HCl

Calculated Values: C, 53.55; H, 7.76; N, 11.35; Cl, 14.37

Measured Values: C, 52.92; H, 7.82; N, 11.22; Cl, 13.88

Figure 5:
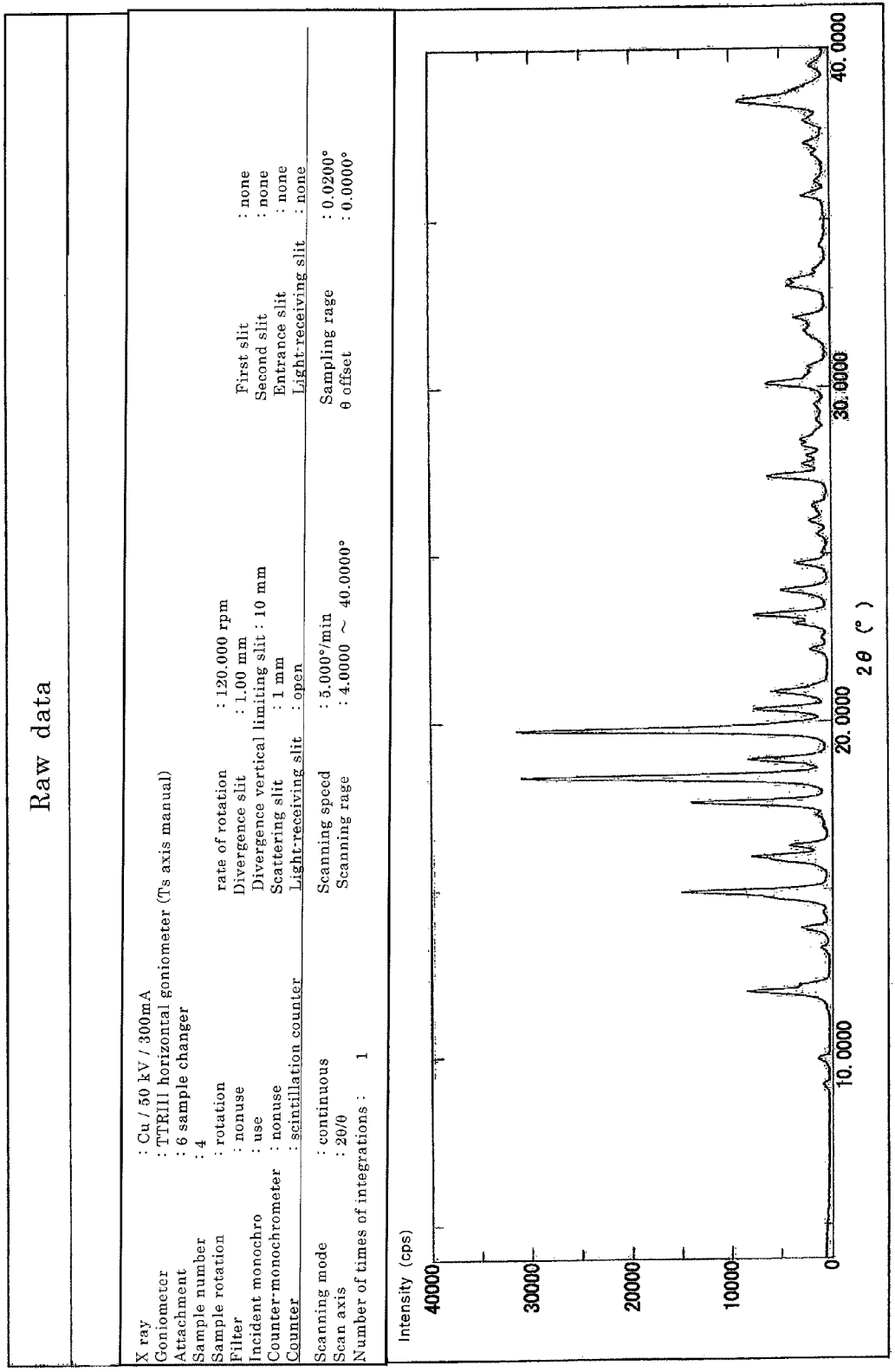
FIG. 5 shows data of powder X-ray diffraction for compound (III-1).
Figure 6:
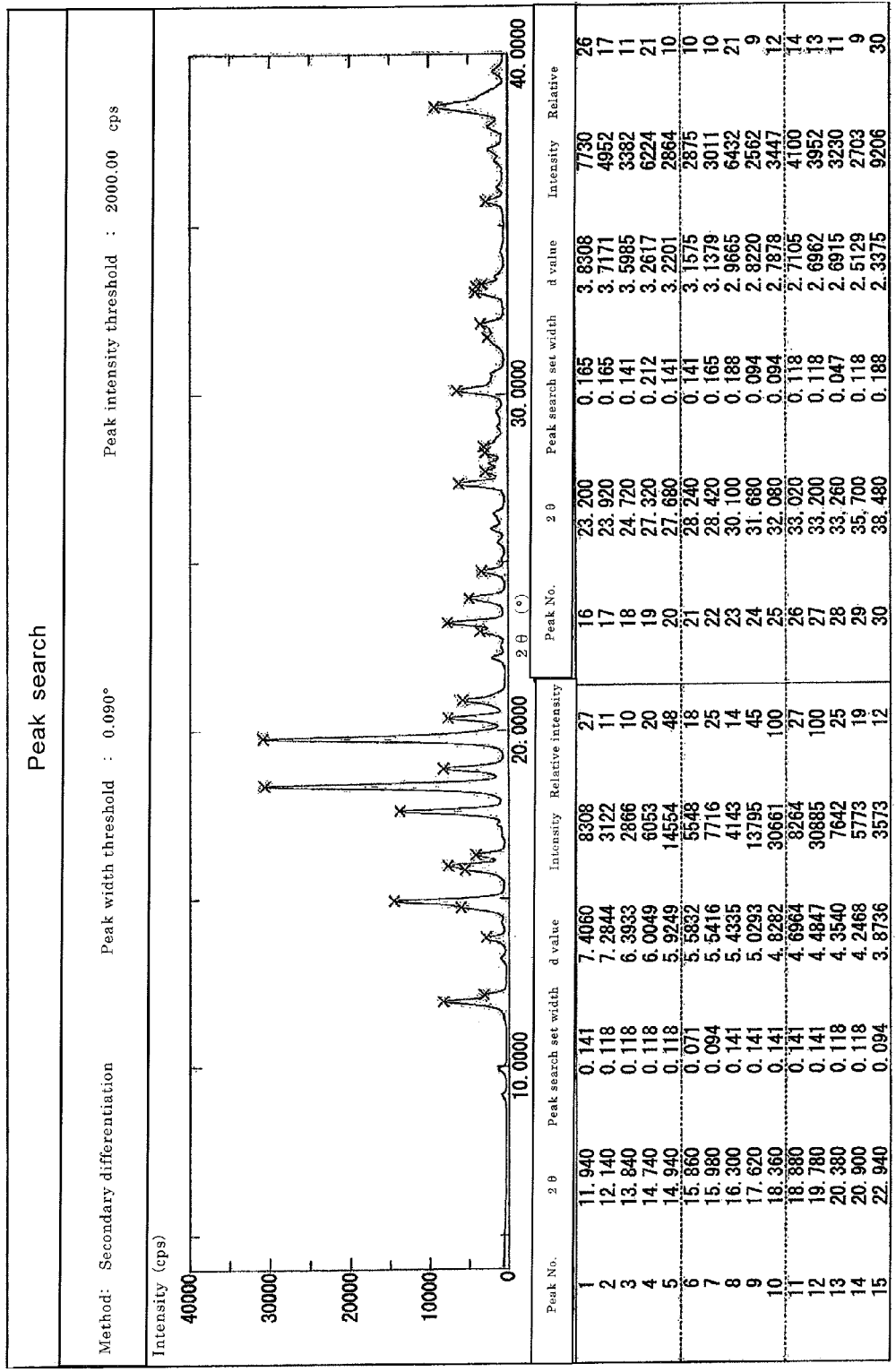
FIG. 6 shows data of powder X-ray diffraction for compound (III-1).

Results of powder X-ray diffraction of Compound III-1 are shown in FIG. 5 and FIG. 6.

Example 4

The melting points were all measured with a melting point measuring device.

(Measuring Conditions)

Device: BUCHI Melting Point B-545

Temperature Rising Rate: PC/min.

Example 5

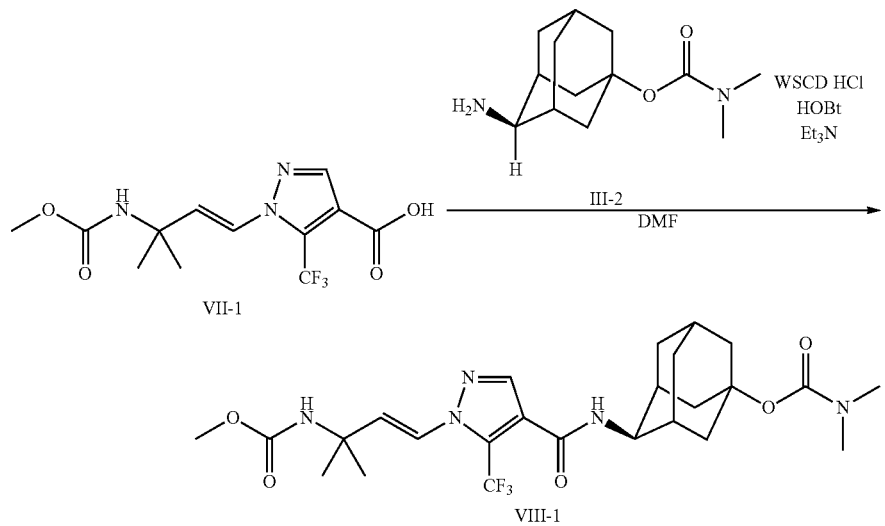

Compound (VII-1) is Compound (II-18) of Example 84 described in WO2008/142986.

To a solution of Compound (VII-1) (100 mg) in dimethylformamide (2.0 ml) were added amine (III-2) (89 mg), 1-(3-dimethylaminopropyl)-3-ethylcarbodiimide hydrochloride (78 mg), 1-hydroxybenzotriazole (12.6 mg) and triethylamine (108 μl), then the reaction mixture was stirred at room temperature for 23 hours. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound (VIII-1) (155 mg, 91.7%).

NMR (d6-DMSO); δ(ppm) 1.40 (s, 8H), 1.88-2.14 (m, 11H), 2.77 (s, 6H), 3.49 (s, 3H), 3.93-4.00 (m, 1H), 6.57 (d, J=13.8 Hz, 1H), 6.88 (d, J=13.8 Hz, 1H), 7.36 (s, 1H), 7.96 (s, 1H), 8.34 (d, J=7.2 Hz, 1H)

Example 6

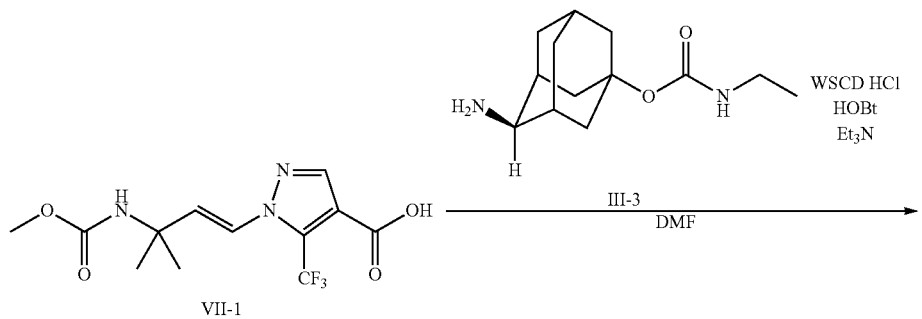

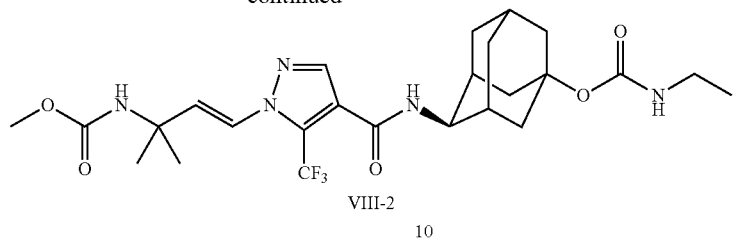

VIII-2

To a solution of Compound (VII-1) (100 mg) in dimethylformamide (2.0 ml) were added amine (III-3) (89 mg), 1-(3-dimethylaminopropyl)-3-ethylcarbodiimide hydrochloride (78 mg), 1-hydroxybenzotriazole (12.6 mg) and triethylamine (108 µl), then the reaction mixture was stirred at room temperature for 20 hours. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound (VIII-2) (122 mg, 72.2%).

NMR (d6-DMSO); δ (ppm) 0.98 (t, J=6.9 Hz, 3H), 1.40 (s, 8H), 1.88-2.13 (m, 11H), 2.88-2.97 (m, 2H), 3.49 (s, 3H), 3.93-3.99 (m, 1H), 6.57 (d, J=13.8 Hz, 1H), 6.81-6.92 (m, 2H), 7.34 (s, 1H), 7.96 (s, 1H), 8.33 (d, J=6.6 Hz, 1H)

Example 7

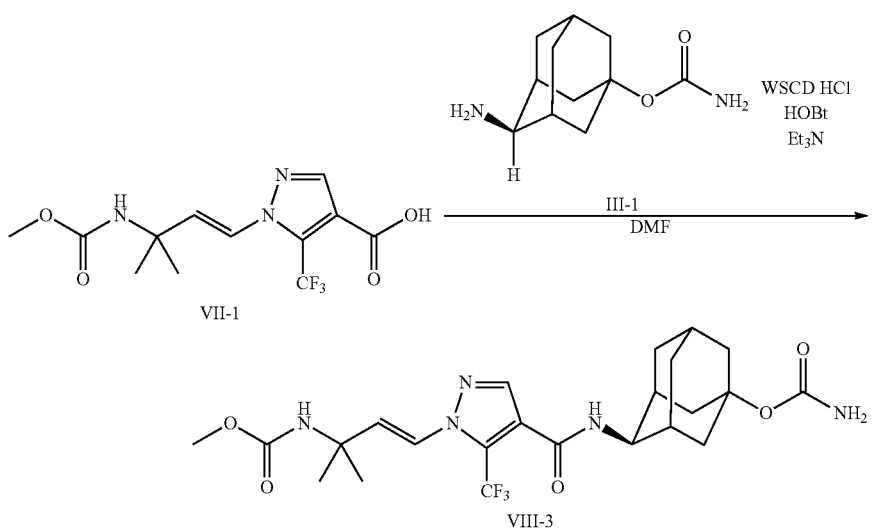

VIII-3

Example 8

To a solution of Compound (VII-1) (100 mg) in dimethylformamide (2.0 ml) were added amine (III-1) (79 mg), 1-(3-dimethylaminopropyl)-3-ethylcarbodiimide hydrochloride (78 mg), 1-hydroxybenzotriazole (12.6 mg) and triethylamine (108 µl), then the reaction mixture was stirred at room temperature for 14 hours. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound (VIII-3) (137 mg, 85.6%).

NMR (d6-DMSO); δ (ppm) 1.40 (s, 8H), 1.88-2.13 (m, 11H), 3.50 (s, 3H), 3.94-3.99 (m, 1H), 6.05-6.35 (s, 2H), 6.58 (d, J=13.6 Hz, 1H), 6.88 (d, J=13.6 Hz, 1H), 7.35 (s, 1H), 7.96 (s, 1H), 8.33 (d, J=6.8 Hz, 1H)

-continued

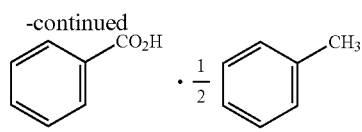

To a solution of adamantanone carbamate (IV-1) (50.00 g, 239.0 mmol) in acetonitrile (300 ml) were added benzylamine (33.30 g, 310.7 mmol) and acetic acid (14.40 g, 239.0 mmol), and the reaction mixture was dissolved at 50° C. The resulting solution was cooled to 5° C., and a solution of sodium borohydride (5.48 g, 143.4 mmol) in N,N-dimethylacetamide solution (100 ml) was added thereto over 1.5 hours. The reaction mixture was stirred for another 1 hour. To the reaction mixture was added 10% hydrochloric acid to obtain pH 1, followed by raising the temperature to room temperature. To the reaction mixture was added 16% sodium hydroxide aqueous solution to obtain pH 9, and was extracted with ethyl acetate. The extracted solution was washed three times with 20% saline, and was concentrated under reduced pressure to 151.07 g. To the concentrated solution were added toluene (400 ml), benzoic acid (20.42 g, 167.3 mmol) and ethyl acetate (175 ml) solution at 25° C. After precipitation of the crystal was confirmed, slurry was concentrated under reduced pressure to 350 ml, and toluene (350 ml) was added. The solution was further concentrated under reduced pressure to 350 ml, and toluene (400 ml) was added. The solution was stirred for 1.5 hours at 25° C., then crystal was filtered, and dried to obtain benzylamino adamantane carbamate toluene-hemisolvated benzoate (II-2) (60.98 g, 54.45%).

Melting Point: 138.4 to 138.7° C.

$^1$H NMR (d6-DMSO); δ (ppm) 1.24-1.34 (brd, 2H), 1.92-2.08 (m, 11H), 2.29 (s, 1.5H), 2.68 (brs, 1H), 3.70 (s, 2H), 7.09-7.37 (m, 7.5H), 7.42-7.51 (m, 2H), 7.54-7.61 (m, 1H), 7.89-7.95 (m, 2H)

Powder X-ray diffraction (toluene-hemisolvated benzoate) 2θ(°); 8.9, 10.1, 12.3, 15.2, 16.3, 18.0, 19.4, 19.7, 20.3, 26.1, 26.4

Element Analysis: $C_{18}H_{24}N_2O_2 \cdot C_7H_6O_2 \cdot \frac{1}{2}C_7H_8$
Calculated Values: C, 74.68; H, 7.44; N, 5.44
Measured Values: C, 72.79; H, 7.40; N, 6.01

Figure 7:
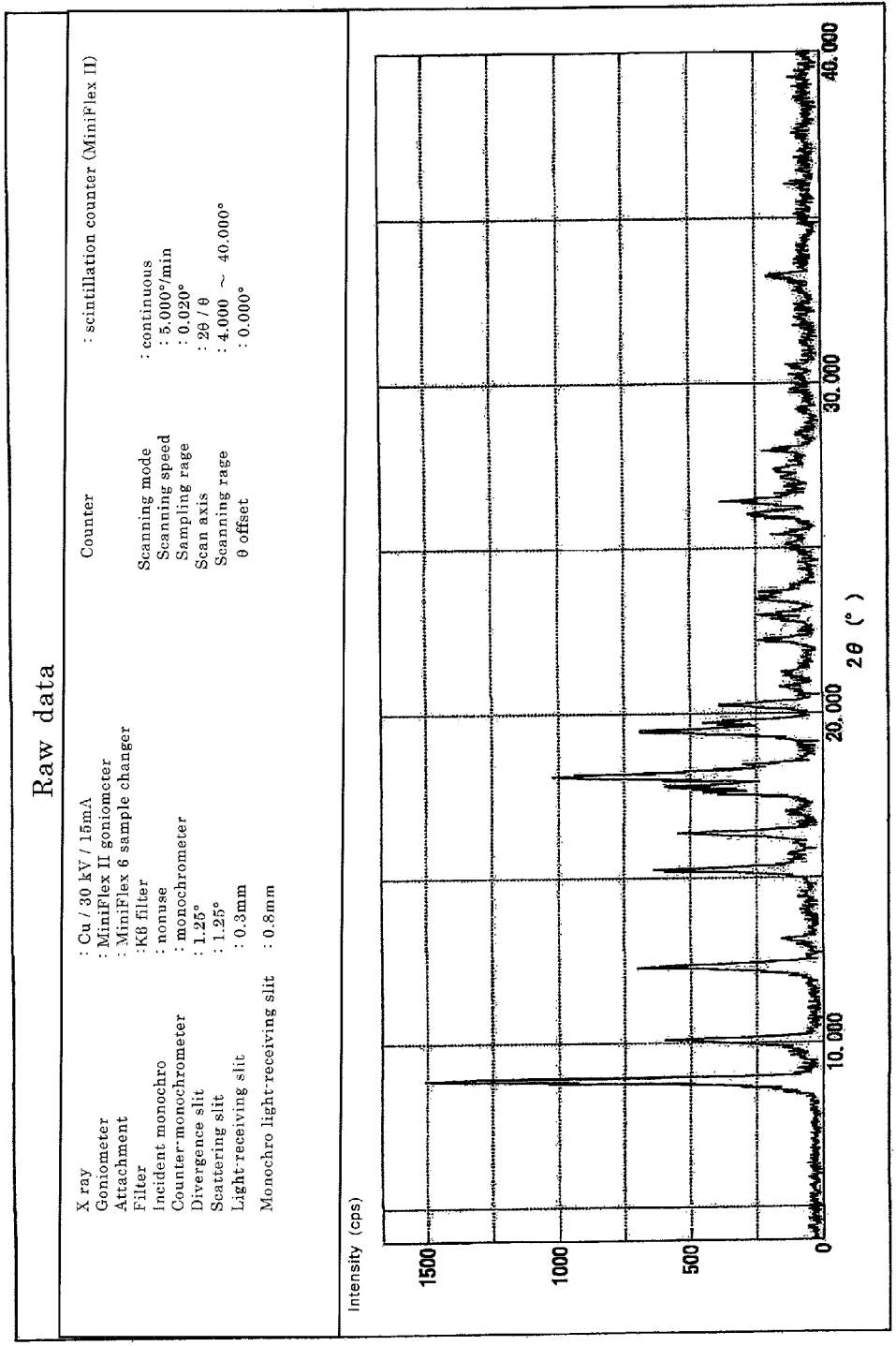
FIG. 7 shows data of powder X-ray diffraction for compound (II-2).
Figure 8:
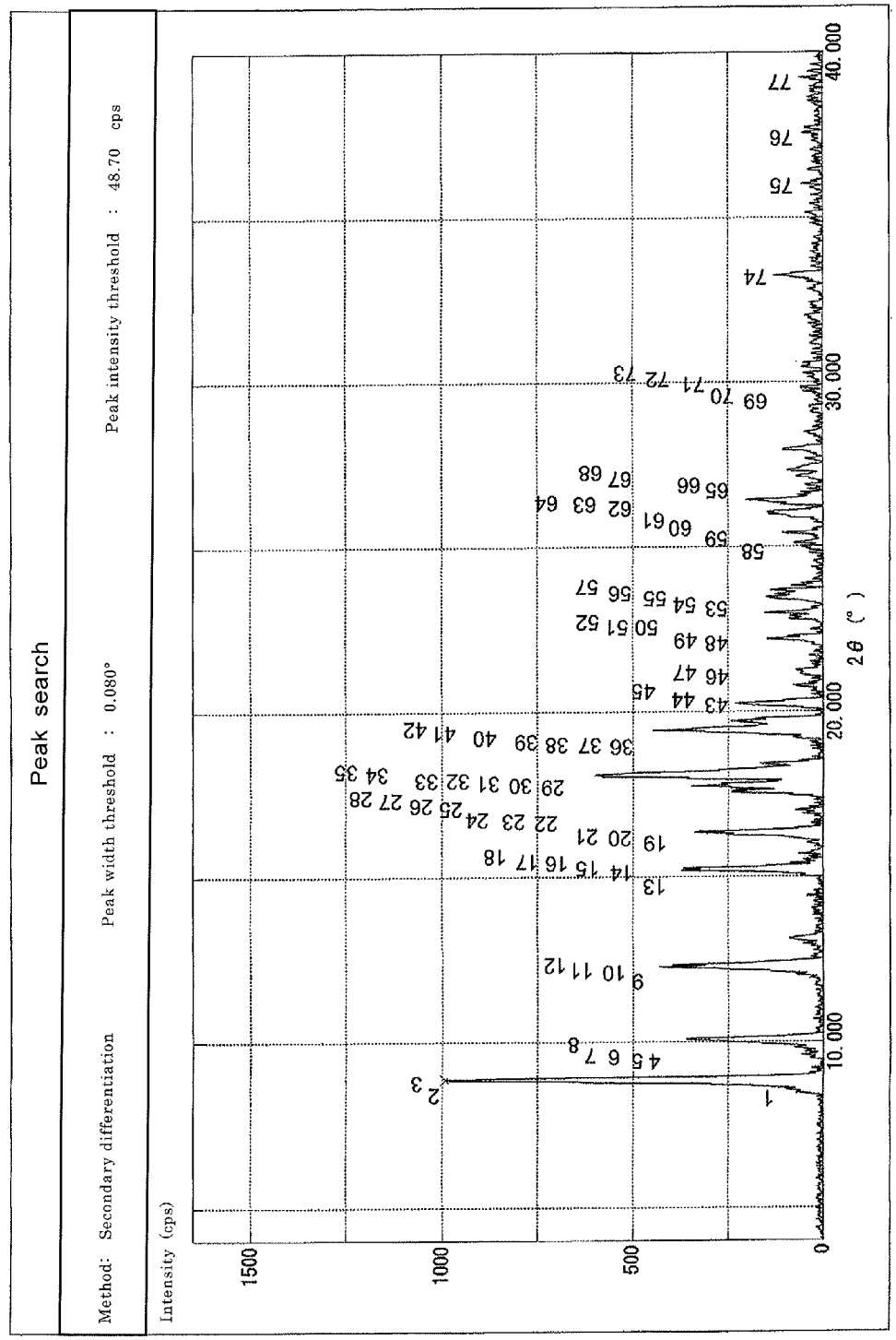
FIG. 8 shows data of powder X-ray diffraction for compound (II-2).

Results of powder X-ray diffraction of Compound (II-2) are shown in FIG. 7 and FIG. 8.

Compound (II-2) exhibited significant purification effects by crystallization, and the ratio of anti isomer to syn isomer was 98 to 2.

Example 9

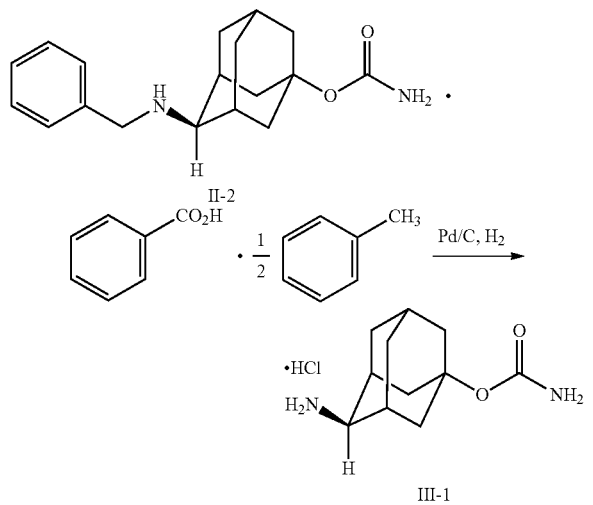

To benzylamino adamantane carbamate toluene-hemisolvated benzoate (II-2) (14.00 g, 29.88 mmol) were added methanol (105 ml) and hydrochloric acid (1.56 g, equivalent to 14.98 mmol of hydrogen chloride, 0.50 equivalents to II-2) to dissolve at 25° C. The reaction mixture was added to methanol (35 ml) slurry of 5% palladium carbon (2.94 g), and catalytic hydrogenation reduction reaction was conducted under hydrogen atmosphere for 3 hours at 40° C. The resulting reaction solution was cooled to 25° C., and 5% palladium carbon was separated by filtration, followed by washing with methanol (14 ml). The resulting filtrate and the washing solution were combined, and hydrochloric acid (1.40 g, equivalent to 13.44 mmol of hydrogen chloride, 0.45 equivalents to II-2) was added thereto. The reaction solution was concentrated under reduced pressure to about 26 g at 40° C. or below. Ethyl acetate (70 ml) was added to the concentrated slurry, and was cooled to 25° C. The slurry was adjusted to pH of 2 or below by hydrochloric acid, then was cooled to 10° C., and was crystallized for 1 hour. The precipitated solid was filtered, and dried to obtain aminoadamantane carbamate hydrochloride (III-1) (6.48 g, 87.9%).

Example 10

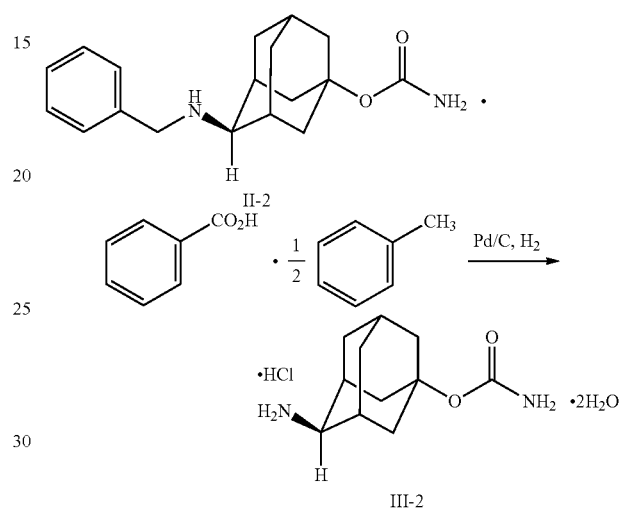

To benzylamino adamantane carbamate toluene-hemisolvated benzoate (II-2) (40.00 g, 85.36 mmol) were added methanol (300 ml) and hydrochloric acid (4.46 g, equivalent to 42.80 mmol of hydrogen chloride, 0.50 equivalents to II-2) to dissolve at 25° C. The solution was added to methanol (100 ml) slurry of 5% palladium carbon (8.40 g), and catalytic hydrogenation reduction reaction was conducted under hydrogen atmosphere for 3 hours at 40° C. The resulting reaction solution was cooled to 25° C., and 5% palladium carbon was separated by filtration, followed by washing with methanol (40 ml). To a reaction mixture (406 g) obtained by combining the resulting filtrate and the washing solution was added hydrochloric acid (4.00 g, equivalent to 38.40 mmol of hydrogen chloride, 0.45 equivalents to II-2). The reaction solution was concentrated under reduced pressure to about 100 ml. To the concentrated slurry were added water (7.2 g, 400 mmol) and ethyl acetate (144 g), and the resulting slurry was concentrated under reduced pressure to about 140 ml. To the concentrated slurry was added ethyl acetate (144 g), and the concentrated slurry was again concentrated under reduced pressure to about 140 ml. The slurry was cooled to 25° C., then ethyl acetate (215 g) was added thereto, followed by adjusting to pH of 2 or below with hydrochloric acid. The slurry was then crystallized for 80 minutes. The precipitated solid was filtered, and dried under reduced pressure at room temperature to obtain aminoadamantane carbamate hydrochloride dihydrate (III-2) (22.85 g, 94.7%).

The aminoadamantane carbamate hydrochloride dihydrate (III-2) is stable to temperature and humidity changes. Thus, it does not need to be stored in the presence of a desiccant agent such as silica gel, or it may be stored without being sealed. Therefore, it is very easy to handle.

NMR data, X-ray diffraction data, element analysis data of aminoadamantane carbamate hydrochloride dihydrate (III-2) are provided below.

$^1$H NMR (d6-DMSO); δ (ppm) 1.45 (brd, J=13 Hz, 2H), 1.97 (brd, J=13 Hz, 2H), 2.05 (m, 1H), 2.06 (br, 1H), 2.08 (brd, J=11 Hz, 2H), 2.12 (brd, J=11 Hz, 2H), 2.19 (br, 2H), 3.29 (m, 1H), 3.35 (br, 4H), 6.24 (br, 2H), 8.31 (brs, 3H)

Powder X-ray diffraction 2θ (°); 14.7, 18.9, 20.9, 25.6, 29.8, 31.6

Element Analysis: $C_{11}H_{18}N_2O_2 \cdot HCl \cdot 2H_2O$
Calculated Values: C, 46.72; H, 8.20; N, 9.91; Cl, 12.54
Measured Values: C, 46.17; H, 8.12; N, 9.83; Cl, 12.67

Figure 9:
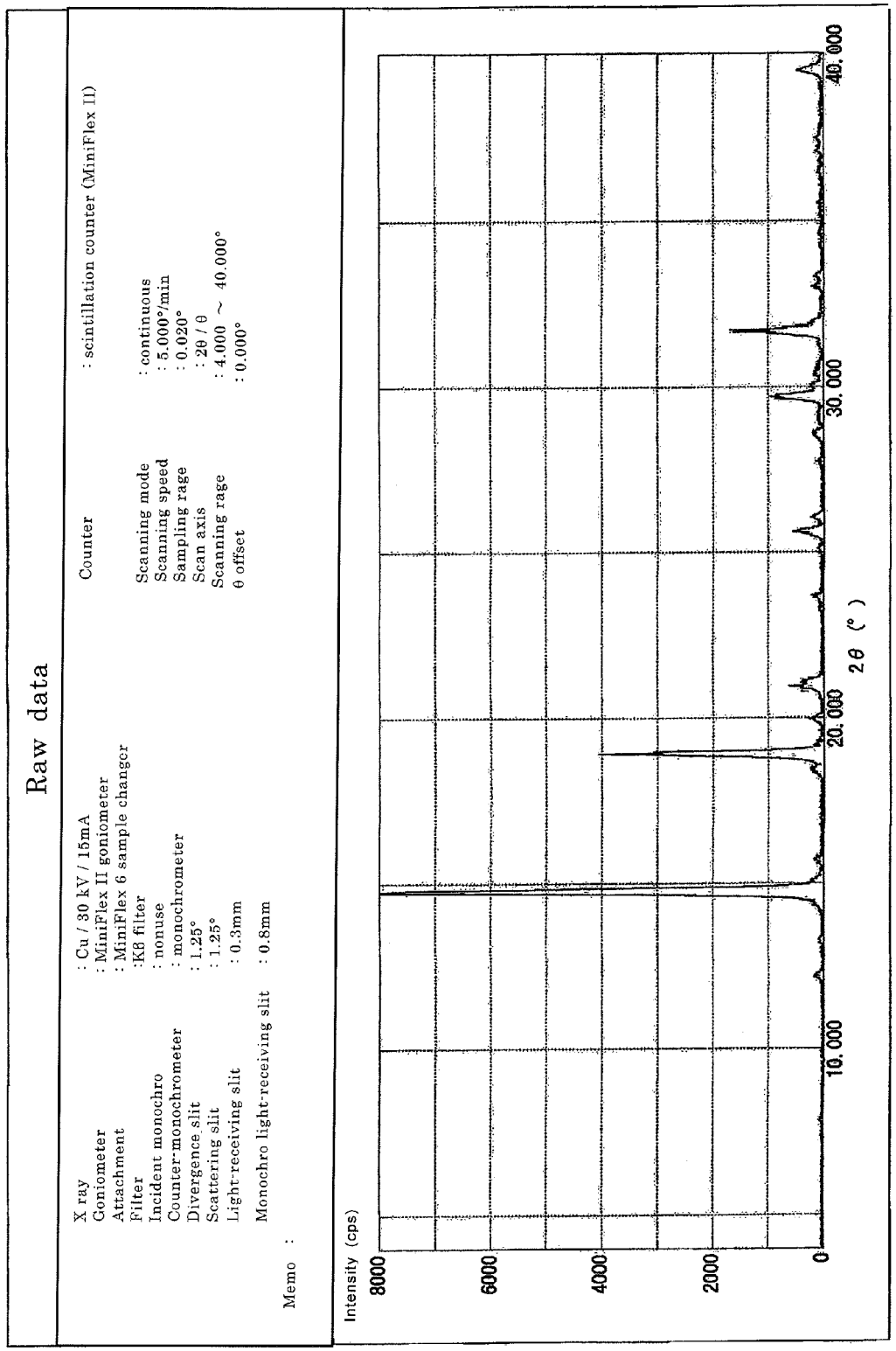
FIG. 9 shows data of powder X-ray diffraction for compound (III-2).
Figure 10:
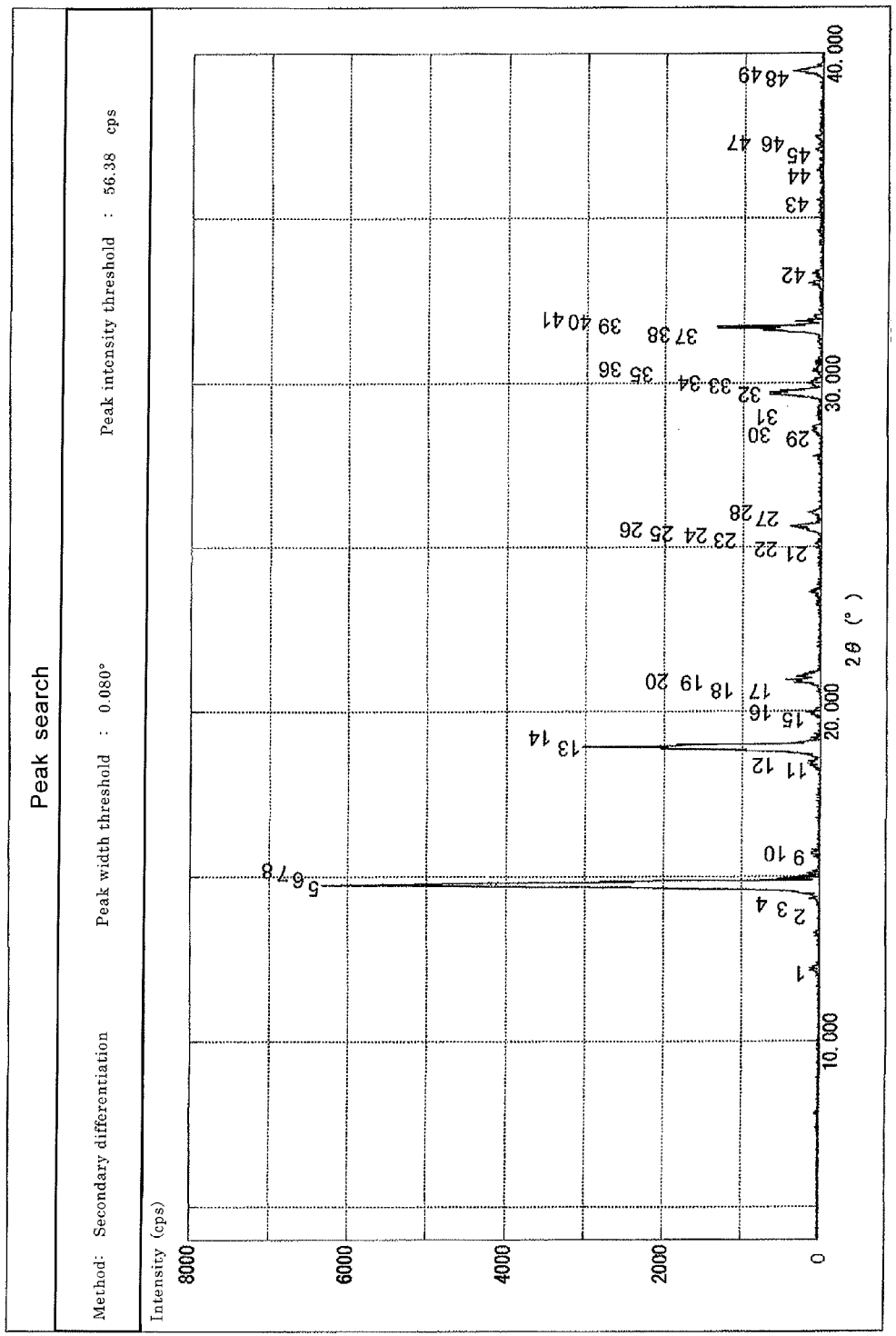
FIG. 10 shows data of powder X-ray diffraction for compound (III-2).

Results of powder X-ray diffraction of aminoadamantane carbamate hydrochloride dihydrate (III-2) are shown in FIG. 9 and FIG. 10.

INDUSTRIAL APPLICABILITY

A compound represented by the Formula (III), its salt, or a solvate thereof is useful as an intermediate to produce a compound represented by the Formula (VIII), its salt, or a solvate thereof. A compound represented by the Formula (II), a compound represented by the Formula (IV), and a compound represented by the Formula (VI) are useful as a material and an intermediate to produce a compound represented by the Formula (III). The process of the present invention enables to produce with efficiency a compound represented by the Formula (VIII).

The invention claimed is:

1. A process for producing an acid addition salt of a compound represented by the Formula (II):

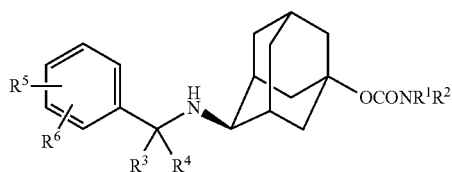

or a solvate of the acid addition salt, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl; which comprises separating an acid addition salt of a compound represented by the Formula (II) or a solvate of the acid addition salt by adding an acid to a mixture of syn isomer and anti isomer of a compound represented by the Formula (I):

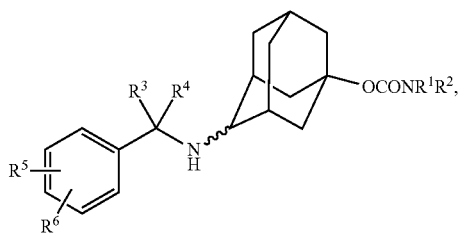

wherein $R^1$, $R^2$, $R^3$, $R^4$, $R^5$ and $R^6$ are as defined above, in the presence of a solvent.

2. The process according to claim 1, which comprises crystallizing an acid addition salt of a compound represented by the Formula (II) or a solvate of the acid addition salt.

3. A process for producing a compound represented by the Formula (III):

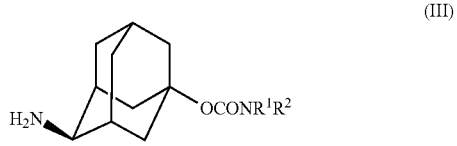

wherein $R^1$ and $R^2$ are as defined in claim 1, its salt, or a solvate thereof, which comprises deprotecting an acid addition salt of a compound represented by the Formula (II):

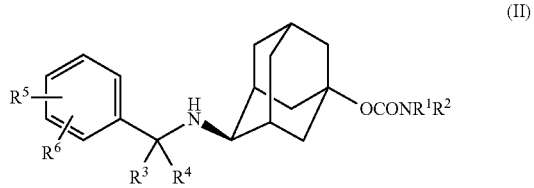

or a solvate of the acid addition salt, wherein $R^1$, $R^2$, $R^3$, $R^4$, $R^5$; and $R^6$ are as defined in claim 1.

4. The process according to claim 3, wherein the deprotection is performed in the presence of an acid.

5. The process according to claim 4, wherein the acid is hydrochloric acid.

6. The process for producing the compound represented by the Formula (III) according to claim 3, its salt, or a solvate thereof, wherein the compound of Formula (II) is produced by a process comprised of separating an acid addition salt of a compound represented by the Formula (II) or a solvate of the acid addition salt by adding an acid to a mixture of syn isomer and anti isomer of a compound represented by the Formula (I).

7. The process according to claim 1, wherein the acid addition salt is hydrochloride.

8. The process according to claim 1, wherein the acid addition salt is benzoate.

9. The process according to claim 1, wherein an acid addition salt of a compound represented by the Formula (II) or a solvate of the acid addition salt is a toluene-solvated benzoate.

10. A process for producing a compound represented by the Formula the (VI):

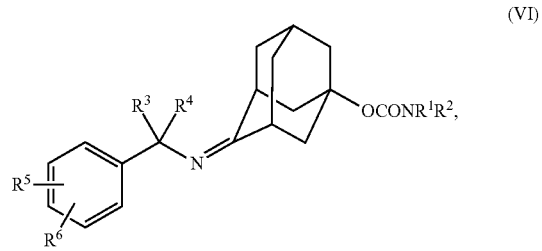

its salt, or a solvate thereof, wherein $R^1$, $R^2$, $R^3$, $R^4$, $R^5$; and $R^6$ are as defined in claim 1 which comprises reacting a compound represented by the Formula (IV):

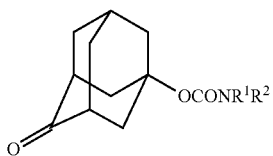

wherein $R^1$ and $R^2$ are as defined in claim 1, and a compound represented by the Formula (V):

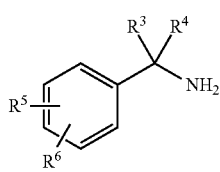

wherein $R^3$, $R^4$, $R^5$ and $R^6$ are as defined in claim 1.

11. A process for producing a compound represented by the Formula (I):

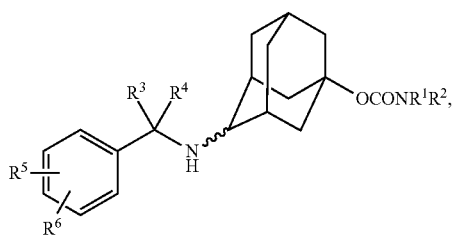

its salt, or a solvate thereof, wherein $R^1$, $R^2$, $R^3$, $R^4$, $R^5$; and $R^6$ are as defined in claim 1, which comprises reducing a compound represented by the Formula (VI):

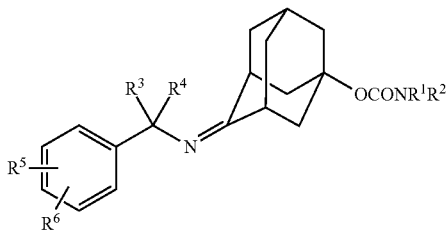

wherein $R^1$, $R^2$, $R^3$, $R^4$, $R^5$ and $R^6$ are as defined in claim 1.

12. The process according to claim 10, wherein the process comprises adding an acid.

13. The process according to claim 11, wherein a hydride reducing agent is used for reducing.

14. The process according to claim 11, wherein the process comprises reduction using one or more reducing agent(s) selected from sodium tri(acetoxy)hydroborate, sodium borohydride, lithium tetrahydroborate, pyridine borane complex, tetrahydrofuran borane complex, dimethyl sulfide borane complex, 2-picoline borane complex and sodium.

15. A process for producing a compound represented by the Formula (IV):

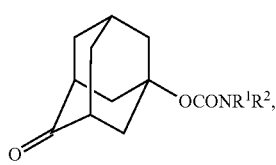

its salt, or a solvate thereof, wherein $R^1$ and $R^2$ are hydrogen, which comprises reacting 5-hydroxy-2-adamantanone and chlorosulfonyl isocyanate, followed by hydrolysis.

16. The process according to claim 6, wherein the compound represented by Formula (I) is produced by reducing a compound represented by the Formula (VI)

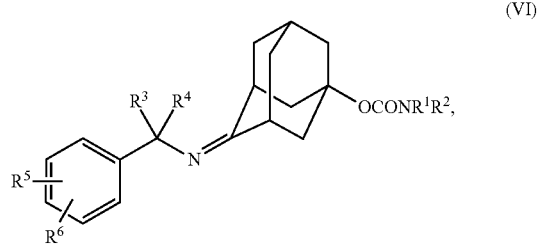

and the compound represented by the Formula (VI) is produced by reacting a compound represented by the Formula (IV):

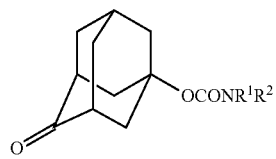

and a compound represented by the Formula (V):

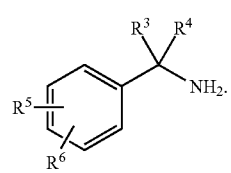

17. The process according to claim 1, wherein $R^3$, $R^4$, $R^5$ and $R^6$ are hydrogen.

18. The process according to claim 1, wherein $R^1$ and $R^2$ are hydrogen.

19. A process for producing a compound represented by the Formula (VIII):

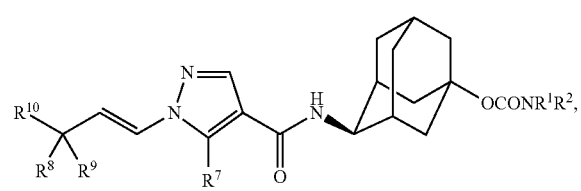

its salt, or a solvate thereof, wherein $R^1$ and $R^2$ are as defined in claim 1;

$R^7$ is a group represented by the formula —Y—$R^{11}$, wherein Y is a single bond, —O— or —S—, and $R^{11}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^8$ and $R^9$ are each independently hydrogen, substituted or unsubstituted alkyl or halogen, or $R^8$ and $R^9$ taken together with the adjacent carbon atom to which they are attached may form a substituted or unsubstituted ring;

$R^{10}$ is
a group represented by the formula —C(=O)—NR$^{12}$R$^{13}$, wherein $R^{12}$ and $R^{13}$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl, or substituted or unsubstituted heterocyclylsulfonyl, or $R^{12}$ and $R^{13}$ taken together with the adjacent nitrogen atom to which they are attached may form a substituted or unsubstituted ring, or a group represented by the formula —NR$^{14}$R$^{15}$, wherein $R^{14}$ and $R^{15}$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl, or substituted or unsubstituted sulfamoyl, or $R^{14}$ and $R^{15}$ taken together with the adjacent nitrogen atom to which they are attached may form a substituted or unsubstituted ring;

which comprises obtaining a compound represented by the Formula (III):

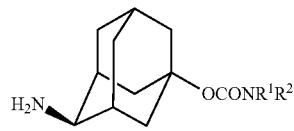

(III)

its salt, or a solvate thereof, wherein $R^1$ and $R^2$ are as defined in claim 1, by the process according to claim 1, followed by reacting the obtained compound represented by the Formula (III) and a compound represented by the Formula (VII):

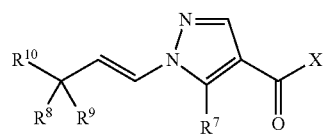

(VII)

wherein $R^7$, $R^8$, $R^9$ and $R^{10}$ are as defined above, X is hydroxy or a leaving group.

20. A compound represented by the Formula (IV):

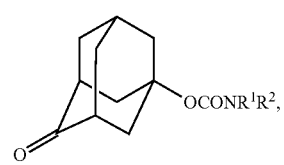

(IV)

its salt, or a solvate thereof, wherein $R^1$ and $R^2$ are each independently hydrogen, substituted or unsubstituted alkyl, or substituted or unsubstituted aryl.

21. A compound represented by the Formula (VI):

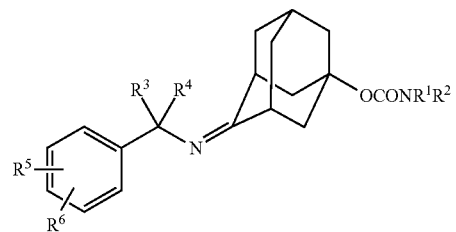

(VI)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, or substituted or unsubstituted alkyloxy, substituted or unsubstituted alkylsulfonyl, substituted or unsubstituted arylsulfonyl, or substituted or unsubstituted sulfamoyl.

22. A compound represented by the Formula (II):

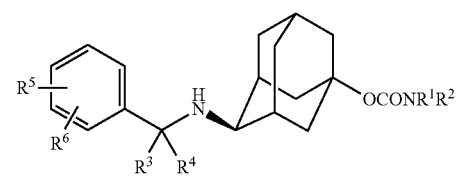

(II)

its salt, or a solvate thereof, wherein $R^1$ and $R^2$ are each independently hydrogen, substituted or unsubstituted alkyl, or substituted or unsubstituted aryl; $R^3$ and $R^4$ are each independently hydrogen, substituted or unsubstituted alkyl, or substituted or unsubstituted aryl; and $R^5$ and $R^6$ are each independently hydrogen, halogen, carboxy, nitro, substituted or unsubstituted alkyl, substituted or unsubstituted alkyloxy, substituted or unsubstituted alkylsulfonyl, substituted or unsubstituted arylsulfonyl, or substituted or unsubstituted sulfamoyl.

23. Hydrochloride of the compound represented by the Formula (II) according to claim 22, or a solvate of the hydrochloride.

24. Benzoate of a compound represented by the Formula (II) according to claim 22, or toluene-solvated benzoate.

25. An acid addition salt of the compound represented by the Formula (III):

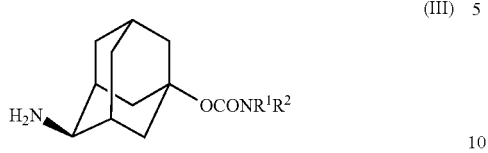

or a solvate of the acid addition salt, wherein $R^1$ and $R^2$ are each independently hydrogen, substituted or unsubstituted alkyl, or substituted or unsubstituted aryl.

26. A hydrochloride of the compound represented by the Formula (III) according to claim 25, or a dihydrate of the hydrochloride.

27. The process according to claim 11, wherein the process comprises adding an acid.

28. The process according to claim 12, wherein a hydride reducing agent is used for reducing.

29. The process according to claim 12, wherein the process comprises reduction using one or more reducing agent(s) selected from sodium tri(acetoxy)hydroborate, sodium borohydride, lithium tetrahydroborate, pyridine borane complex, tetrahydrofuran borane complex, dimethyl sulfide borane complex, 2-picoline borane complex and sodium.

* * * * *